United States Patent
Siankevich et al.

(10) Patent No.: US 11,925,925 B2
(45) Date of Patent: Mar. 12, 2024

(54) IONIC POLYMERS AND USE THEREOF IN BIOMASS PROCESSING

(71) Applicant: EMBION TECHNOLOGIES SA, Ecublens (CH)

(72) Inventors: Sviatlana Siankevich, Chavannes-près-Renens (CH); Georgios Savoglidis, Chavannes-près-Renens (CH); Paul Joseph Dyson, Ecublens (CH); Zhaofu Fei, Kaiseraugst (CH)

(73) Assignee: Embion Technologies SA, Ecublens (CH)

(*) Notice: Subject to any disclaimer, the term of this patent is extended or adjusted under 35 U.S.C. 154(b) by 241 days.

(21) Appl. No.: 16/648,351

(22) PCT Filed: Sep. 19, 2018

(86) PCT No.: PCT/IB2018/057206
§ 371 (c)(1),
(2) Date: Mar. 18, 2020

(87) PCT Pub. No.: WO2019/058270
PCT Pub. Date: Mar. 28, 2019

(65) Prior Publication Data
US 2020/0246785 A1    Aug. 6, 2020

Related U.S. Application Data

(63) Continuation of application No. PCT/IB2017/055670, filed on Sep. 19, 2017.

(51) Int. Cl.
| | | |
|---|---|---|
| B01J 31/08 | (2006.01) | |
| C07D 307/50 | (2006.01) | |
| C07H 1/08 | (2006.01) | |
| C07H 3/02 | (2006.01) | |
| C07H 3/04 | (2006.01) | |
| C07H 3/06 | (2006.01) | |
| C08F 226/06 | (2006.01) | |

(52) U.S. Cl.
CPC ............ *B01J 31/08* (2013.01); *C07D 307/50* (2013.01); *C07H 1/08* (2013.01); *C07H 3/02* (2013.01); *C07H 3/04* (2013.01); *C07H 3/06* (2013.01); *C08F 226/06* (2013.01); *B01J 2231/60* (2013.01); *B01J 2531/002* (2013.01)

(58) Field of Classification Search
CPC ...... B01J 31/08; B01J 13/14; B01J 2531/002; C08F 26/06; C07C 69/54; C07C 67/26; C07C 31/20; C07C 29/10
USPC ...... 526/263, 295, 100; 525/327.1; 524/269, 524/548
See application file for complete search history.

(56) References Cited

U.S. PATENT DOCUMENTS

| | | | | |
|---|---|---|---|---|
| 8,030,030 | B2* | 10/2011 | Varanasi | C12P 19/14 435/72 |
| 8,575,374 | B1* | 11/2013 | DeLong | C07D 233/60 549/548 |
| 10,894,851 | B2* | 1/2021 | Dyson | D21C 11/0007 |
| 2002/0028887 | A1* | 3/2002 | Hirano | C08F 226/06 526/263 |
| 2010/0319862 | A1 | 12/2010 | Rahman | |
| 2016/0032038 | A1* | 2/2016 | Baynes | C08F 8/36 127/29 |

FOREIGN PATENT DOCUMENTS

| | | |
|---|---|---|
| CN | 106632164 A | 5/2017 |
| WO | 2006/053083 A2 | 5/2006 |
| WO | 2009/114830 A2 | 9/2009 |
| WO | 2013/066941 A1 | 5/2013 |
| WO | 2017/158117 A1 | 9/2017 |

OTHER PUBLICATIONS

Pourjavadi et al., Journal of Molecular Catalysis A: Chemical, 2012, 365, 55-59.*
International Search Report and Written Opinion for PCT/IB2018/057206 dated Mar. 28, 2019.

* cited by examiner

*Primary Examiner* — Ganapathy Krishnan
(74) *Attorney, Agent, or Firm* — Weston R. Gould; Dinsmore & Shohl LLC

(57) ABSTRACT

The invention provides ionic polymers (IP) consisting of anions and a polymeric backbone containing cations. The invention also provides the ionic polymers incorporated in membranes or attached to solid supports and use of the ionic polymers in processing of biomass.

22 Claims, 7 Drawing Sheets

IONIC POLYMERS AND USE THEREOF IN BIOMASS PROCESSING

FIELD OF THE INVENTION

The invention provides ionic polymers (IP) consisting of anions and a polymeric backbone containing cations. The invention also provides the ionic polymers incorporated in membranes or attached to solid supports and use of the ionic polymers in processing of biomass.

BACKGROUND OF THE INVENTION

Lignocellulosic biomass (or simply biomass) is comprised primarily of cellulose, hemicellulose and lignin, which, depending on the biomass type, are cross-linked, trapped or even non-covalently attached to each other or covalently attached to each other by acidic residues. The selective cleavage of chemical bonds results in formation of different types of poly and/or oligosaccharides, e.g. β-glucan, fructan, xylan, arabinoxylan, mannan, galactan or combination of thereof with variable degree of polymerization.

Polyphenols and carbohydrates including some polysaccharides and oligosaccharides which are selectively utilized by host microorganism conferring a health benefit are known as prebiotic (Glenn R. Gibson, Nature Reviews Gastroenterology & Hepatology volume 14, pages 491-502 (2017)). Most oligosaccharides used as prebiotics at present are produced by hydrolysis from natural sources, obtained by hydrothermal, an enzymatic or acid/base hydrolysis of polysaccharides and combinations thereof.

The extraction of oligosaccharides by hydrothermal hydrolysis usually requires the release of polysaccharides from the raw material, followed by depolymerisation, however, high temperature (>190° C.) is often used and side products of sugar dehydration are being formed. The main drawback of the chemical solvents methods is that the hydrolysis of oligomers is unsustainable and requires costly removal of the chemicals by extensive dialysis or ultrafiltration. Additionally, formation of byproducts is observed due to the uncontrolled lysis of the cell walls polymeric structures.

Enzymatic hydrolysis can be more targeted avoiding some of the byproducts formation of the other two processes but efficiency of the process is much lower with long reaction times, additional pre-treatment and post-treatment required as well as lower yield and productivity.

Purity of enzymes used is also an issue with the observation of background activities that result in byproduct formation. Finally, because of all these drawbacks, enzymatic hydrolysis for prebiotics production process are usually more expensive than traditional water and acid/base hydrolysis.

As alternatives to conventional mineral acid hydrolysis several other approaches exist such as the application of solid acid catalysts, which is seen to be more environmentally friendly as they simplify downstream processing. For instance, sulfonic acid (—$SO_3H$) functionalized solid catalysts exhibit highly efficient catalytic performance for cellulose hydrolysis and show different catalytic effects depending on the morphology of the support.

As further alternatives, ionic liquids (ILs) have been utilized in the processing of biomass. The studies demonstrated the benefits of using an ionic liquid in the hydrolysis of cellulose. The dissolution of the cellulose allows for increased reaction rates due to the accessibility of the glucosidic bonds in the cellulose. Another report suggested the use of ILs, again as a solvent for cellulose, but with solid acid catalysts for the hydrolysis of cellulose. While this system demonstrated the ability to convert cellulose to simple sugars, heterogeneous catalysis can have low yields due to inefficient mixing. US 2010/0319862 A1 (The Board of Trustees of the University of Alabama) discloses methods involving multiphasic (e.g., biphasic) compositions comprising an ionic liquid (IL) and a fractionation polymer, such as a polyalkylene glycol, in the substantial absence of water for processing biomass.

Recently ILs containing acidic units have shown high performance in selectively deconstructing biomass and also in the simultaneous catalytic conversion of the constituents. For example, U.S. Pat. No. 8,575,374 B1 (DeLong et al.) discloses that the depolymerization method involves dissolving the biomass in a homogeneous solution comprising an ionic liquid solvent and an ionic liquid catalyst as a depolymerization catalyst. The depolymerization reaction rates are facilitated by heating and stirring of the ionic liquid solvent and ionic liquid catalyst solution. However, the major drawback during the hydrolysis with solid acids and/or ILs is leaching and/or difficulties in separation, which limits their application.

For the preparation of food-grade products for human or animal consumption, ionic liquid and/or other conventional catalyst contamination of products is a serious issue. Leaching of the catalyst into the product would implicate a time-consuming and costly cleaning step, which would make the whole process of preparation of food grade and human consumption products more expensive. Indeed, separation of ILs from products can be complicated and can result in increased costs in separation processes. In addition, even if a complete removal of ILs and/or other conventional catalyst is achieved, there is still a risk that such products would never qualify as food grade in certain markets due to severe food legislations. In order to facilitate the recovery of ILs from the mixture, polymers of the components of ILs or so-called ionic polymers (IP) or solid supported ILs have been proposed in the literature for different applications. For example, the sponge-like polymer PDVB-$SO_3H$—[$C_3$vim][$CF_3SO_3$] obtained by co-polymerization of divinylbenzene (DVB) with 1-vinylimidazole and sodium p-styrenesulfonate at 100° C., followed by reaction with 1,3-propane sultone and ion exchange with $CF_3SO_3H$ has been found to be an efficient catalyst for the deconstruction of crystalline cellulose into sugars in ILs (Fujian Liu et al., Depolymerization of crystalline cellulose catalysed by acidic ionic liquids grafted onto sponge-like nanoporous polymers, Chem. Commun., 2013, 49, 8456-8458). However, there is still possible problem of leaching.

Therefore, there is still a need for highly catalytically active ionic polymers (IPs), without leaching of their components in the medium, that are simple and safe for use in processing of biomass. Specific structural design and appropriate selection of the anion should be a key point to achieve such goal.

SUMMARY OF THE INVENTION

An aspect of the present invention provides an ionic polymer (IP) consisting of a first monomer of formula I

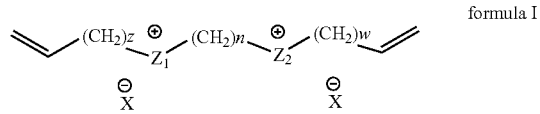

formula I or consisting of a first monomer of formula I

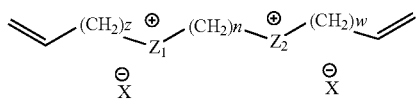

formula I and at least one second monomer selected from the group consisting of

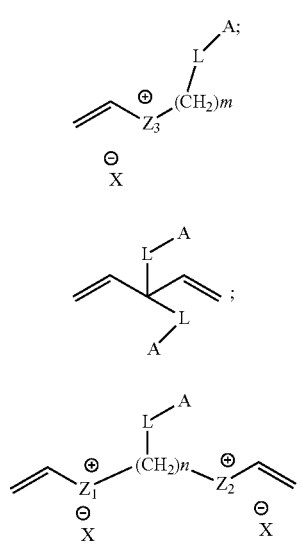

formula II formula III formula IV wherein
n and m are independently selected from 1, 2, 3, 4, 5, 6;
z and w are independently selected from 0, 1, 2;
$Z_1$, $Z_2$ and $Z_3$ are cations each independently selected from the group comprising:

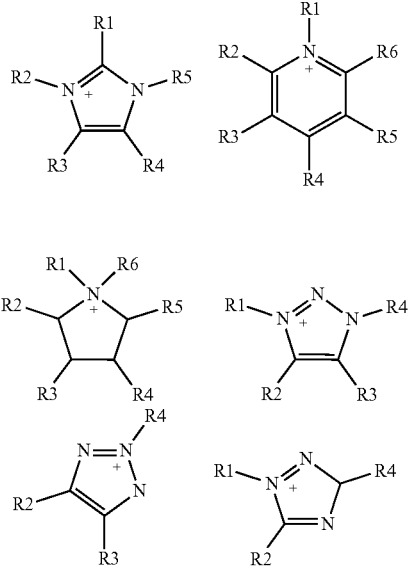

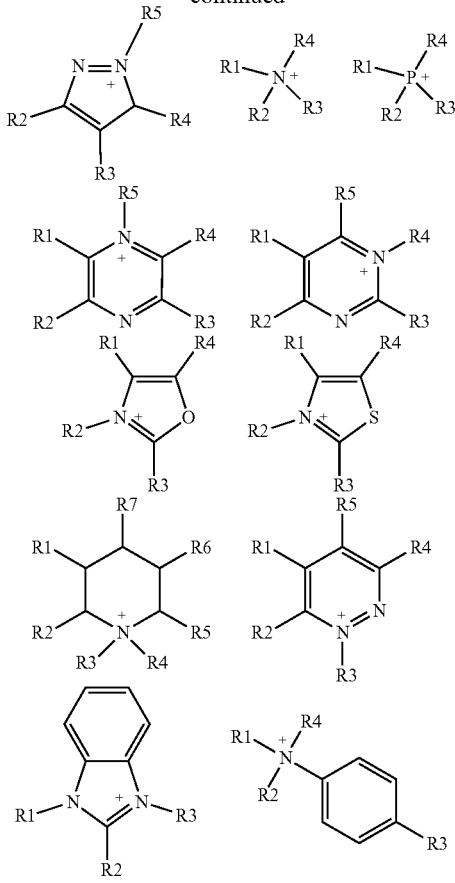

R1, R2, R3, R4, R5, R6 and R7 are each independently selected from the group comprising a bond, H, $C_1$-$C_6$ alkyl, allyl, $CH_3$—$(CH_2)$p-O—$(CH_2)$q-$CH_3$, $C_1$-$C_6$ alkoxy, $C_1$-$C_6$ alkoxyalkyl, benzyl, —$SO_3H$, —$(CH_2)$q-$SO_3H$, provided that two of R1, R2, R3, R4, R5, R6 and R7 are each a bond;
p and q are independently selected from 0, 1, 2, 3, 4, 5, 6;
L is an optional linker and each occurrence of L, if present, is independently selected from substituted or unsubstituted $C_1$-$C_{20}$ alkylene, alkenylene, alkynylene and substituted or unsubstituted $C_5$-$C_{10}$ aryl, wherein the substituents are selected from the group comprising H, —$SO_3H$, —COOH, —[P(=O)(OH)$_2$], —[P(=O)(OH)], —O—$SO_3H$, —O—COOH, —O—[P(=O)(OH)$_2$], —O—[P(=O)(OH)];
A is an optional acidic group and each occurrence of A, if present, is independently selected from the group comprising H, —$SO_3H$, —COOH, —[P(=O)(OH)$_2$], —[P(=O)(OH)], —O—$SO_3H$, —O—COOH, —O—[P(=O)(OH)$_2$], —O—[P(=O)(OH)], —$CH_2$—COOH;
$X^-$ is selected from the group comprising $F^-$, $Cl^-$, $Br^-$, $I^-$, $ClO_4^-$, $BF_4^-$, $PF_6^-$, $AsF_6^-$, $SbF_6^-$, $NO_2^-$, $NO_3^-$, $HSO_4^-$, $SO_4^{2-}$, $PO_4^{3-}$, $HPO_4^{2-}$, $CF_3CO_2^-$, $CF_3CO_3^-$, $CO_3^{2-}$, $CF_3SO_3^-$, $C_1$-$C_6$ carboxylate, $CN^-$, $SCN^-$, $OCN^-$, $CNO^-$, $N_3^-$, tosylate, mesylate, trifluoromethanesulfonate, trifluoroethane sulfonate, di-trifluoromethanesulfonyl amino, docusate, xylenesulfonate;

A further aspect of the present invention provides an ionic polymer network comprising cross-linked one or more ionic polymers of the present invention.

Another aspect of the present invention provides a solid support having at least one surface comprising one or more ionic polymers of the present invention or the ionic polymer network of the present invention.

Another aspect of the present invention provides a polymer membrane incorporating one or more ionic polymers of the present invention or the ionic polymer network of the present invention.

Another aspect of the present invention provides use of ionic polymers of the present invention or a combination thereof, the ionic polymer network of the present invention, the solid support of the present invention or the polymer membrane of the present invention to produce fine chemicals from biomass.

Another aspect of the present invention provides a method for producing one or more fine chemicals selected from the group comprising lipids, sugars, furanic compounds, humins, polyphenols and/or pectic compounds from biomass, the method comprising the steps of:
  a) providing biomass;
  b) optionally determining lipids and/or sugars contents in the biomass;
  c) optionally pretreating the biomass;
  d) contacting the biomass with a catalyst to form a reaction mixture, wherein the catalyst is an ionic polymer of the present invention or a combination of ionic polymers of the present invention, the ionic polymer network of the present invention, a solid-supported ionic polymers of the present invention and/or a membrane of the present invention;
  e) degrading the biomass in the reaction mixture to produce a liquid phase and a solid phase, wherein the liquid phase includes the one or more fine chemicals, and the solid phase includes residual biomass;
  f) isolating at least a portion of the liquid phase from the solid phase; and
  g) recovering the one or more fine chemicals from the isolated liquid phase.

Another aspect of the present invention provides a method for producing C5 and C6 sugars, furfural, 5-hydroxymethylfurfural (HMF) and derivatives of HMF from biomass, the method comprising the steps of:
  a) providing biomass;
  b) optionally determining sugars contents in the biomass;
  c) optionally pretreating the biomass;
  d) contacting the biomass with a catalyst to form a reaction mixture, wherein the catalyst is an ionic polymer of the present invention or a combination of ionic polymers of the present invention, the ionic polymer network of the present invention, a solid-supported ionic polymers of the present invention and/or a membrane of the present invention;
  e) degrading the biomass in the reaction mixture to produce a first liquid phase and a first solid phase, wherein the first liquid phase includes C5 oligomer sugars and/or C5 monomer sugars and can further include furfural if the time of degrading step is extended, and the first solid phase includes residual material;
  f) isolating at least a portion of the first liquid phase from the first solid phase;
  g) recovering C5 oligomer sugars and/or C5 monomer sugars and/or furfural from the isolated first liquid phase;
  h) contacting the first solid phase that includes residual material with the same catalyst as in step d) or with a different catalyst, to form a reaction mixture, wherein the catalyst is an ionic polymer of the present invention or a combination of ionic polymers of the present invention, the ionic polymer network of the present invention, a solid-supported ionic polymers of the present invention and/or a membrane of the present invention;
  i) further degrading the first solid phase that includes residual material in the reaction mixture to produce a second liquid phase and a second solid phase, wherein the second liquid phase includes C6 oligomer sugars and/or C6 monomer sugars and can further include 5-hydroxymethylfurfural (HMF) and derivatives of HMF and/or humins if the time of degrading step is extended, and the second solid phase includes residual material;
  j) isolating at least a portion of the second liquid phase from the second solid phase; and
  k) recovering C6 oligomer sugars and/or C6 monomer sugars and/or 5-hydroxymethylfurfural (HMF) and derivatives of HMF and/or humins from the isolated second liquid phase.

DETAILED DESCRIPTION OF THE INVENTION

Figure 1:
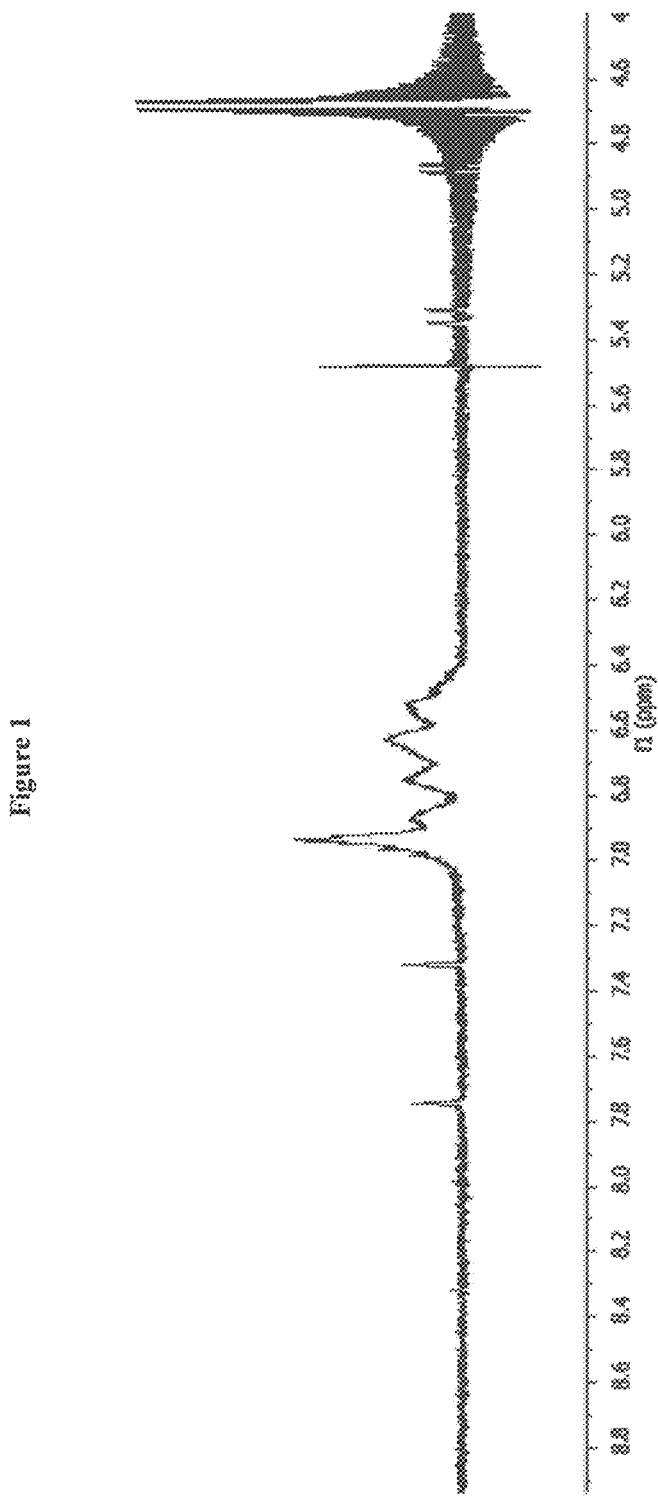
FIG. 1 shows $^1$H NMR spectra of reaction of polymer from the prior art (US20160032038A1).

All publications, patent applications, patents, and other references mentioned herein are incorporated by reference in their entirety. The publications and applications discussed herein are provided solely for their disclosure prior to the filing date of the present application. Nothing herein is to be construed as an admission that the present invention is not entitled to antedate such publication by virtue of prior invention. In addition, the materials, methods, and examples are illustrative only and are not intended to be limiting.

In the case of conflict, the present specification, including definitions, will control. Unless defined otherwise, all technical and scientific terms used herein have the same meaning as is commonly understood by one of skill in art to which the subject matter herein belongs. As used herein, the following definitions are supplied in order to facilitate the understanding of the present invention.

The term "comprise" is generally used in the sense of include, that is to say permitting the presence of one or more features or components. Also as used in the specification and claims, the language "comprising" can include analogous embodiments described in terms of "consisting of" and/or "consisting essentially of".

As used in the specification and claims, the singular form "a", "an" and "the" include plural references unless the context clearly dictates otherwise.

As used in the specification and claims, the term "and/or" used in a phrase such as "A and/or B" herein is intended to include "A and B", "A or B", "A", and "B".

An "allyl" group is a substituent with the structural formula $H_2C=CH-CH_2R$, where R is the rest of the molecule.

The term "monomer" refers to a molecule that can undergo polymerization or copolymerization thereby contributing constitutional units to the essential structure of a macromolecule (a polymer).

"Cross-linking", as used herein, refers to the attachment of two or more monomers, oligomers or longer polymer chains by bridges of a cross-linker, such as an element, molecular group, a compound, or another oligomer or polymer. Cross-linking can result in a polymeric network (which can be two-dimensional or three-dimensional) where the polymer subunits are interconnected with multiple cross-linking agents and without free ends. Cross-linking may take place upon exposure to a stimulus, such as heat or light. As a result, some cross-linking processes occur at increased temperature, and some may also occur at room temperature or at lower temperature. As cross-linking density is increased, the properties of a material can be changed from thermoplastic to thermosetting.

An aspect of the invention provides ionic polymers consisting of anions and a polymeric backbone containing cations. Specifically, the invention provides an ionic polymer (IP) consisting of a first monomer of formula I

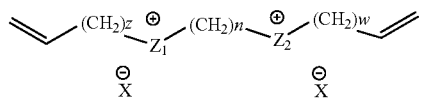

formula I or consisting of a first monomer of formula I

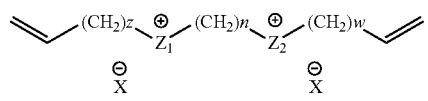

formula I and at least one second monomer selected from the group consisting of

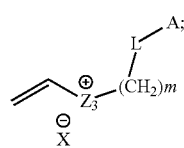

formula II

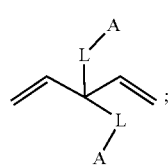

formula III

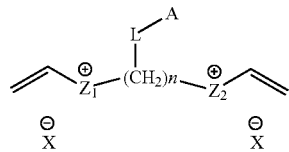

formula IV wherein n and m are independently selected from 1, 2, 3, 4, 5, 6; preferably n and m are independently selected from 1, 2, 3; most preferably n is 2 and m is 1 or 2.

z and w are independently selected from 0, 1, 2, 3; preferably z and w are independently selected from 0 and 1; most preferably z and w are 0 or 1.

$Z_1$, $Z_2$ and $Z_3$ are cations each independently selected from the group comprising:

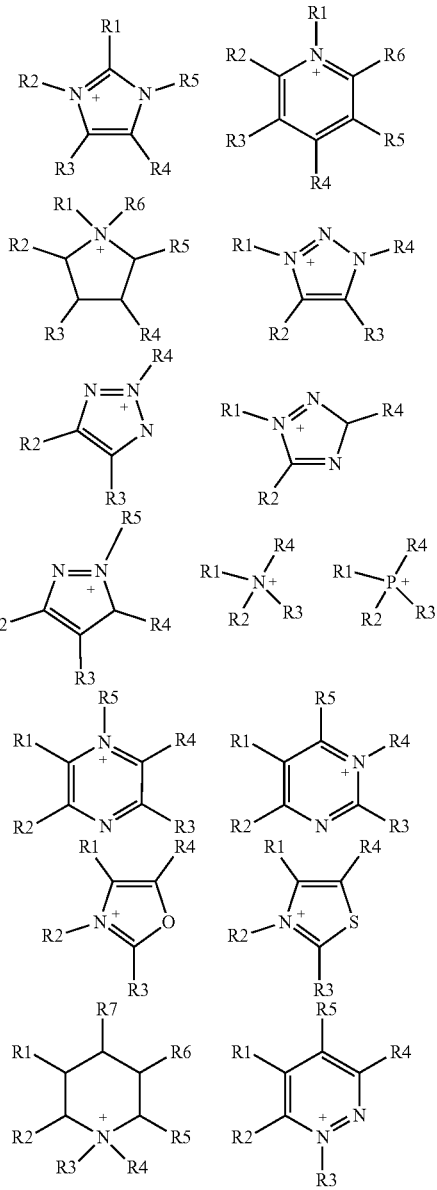

-continued

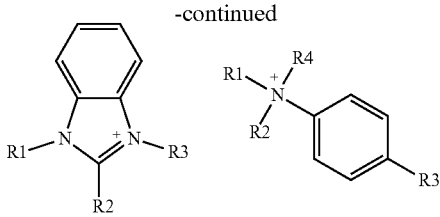

preferably $Z_1$, $Z_2$ and $Z_3$ are cations each independently selected from the group comprising:

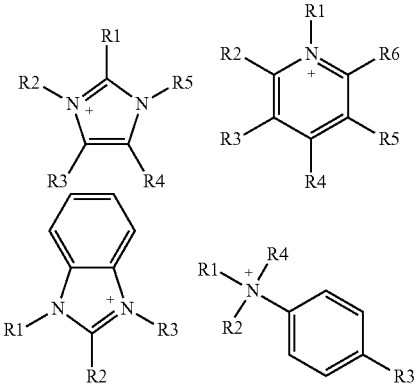

most preferably $Z_1$, $Z_2$ and $Z_3$ are cations each independently selected from the group comprising:

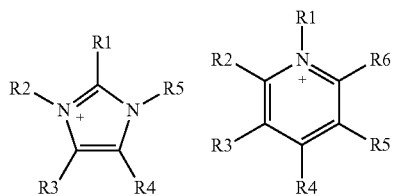

R1, R2, R3, R4, R5, R6 and R7 are each independently selected from the group comprising a bond, H, $C_1$-$C_6$ alkyl, allyl, $CH_3$—$(CH_2)$p-O—$(CH_2)$q-$CH_3$, $C_1$-$C_6$ alkoxy, $C_1$-$C_6$ alkoxyalkyl, benzyl, —$SO_3H$, —$(CH_2)$q-$SO_3H$, provided that two of R1, R2, R3, R4, R5, R6 and R7 are each a bond; preferably R1, R2, R3, R4, R5, R6 and R7 are each independently selected from the group comprising a bond, H, $C_1$-$C_6$ alkyl, provided that two of R1, R2, R3, R4, R5, R6 and R7 are each a bond; most preferably R1, R2, R3, R4, R5, R6 and R7 are each independently selected from the group comprising a bond and H, provided that two of R1, R2, R3, R4, R5, R6 and R7 are each a bond;

p and q are independently selected from 0, 1, 2, 3, 4, 5, 6;

L is an optional linker and each occurrence of L, if present, is independently selected from substituted or unsubstituted $C_1$-$C_{20}$ alkylene, alkenylene, alkynylene and substituted or unsubstituted $C_5$-$C_{10}$ aryl, wherein the substituents are selected from the group comprising H, —$SO_3H$, —COOH, —[P(=O)(OH)$_2$], —[P(=O)(OH)], —O—$SO_3H$, —O—COOH, —O—[P(=O)(OH)$_2$], —O—[P(=O)(OH)], preferably L is absent;

A is an optional acidic group and each occurrence of A, if present, is independently selected from the group comprising H, —$SO_3H$, —COOH, —[P(=O)(OH)$_2$], —[P(=O)(OH)], —O—$SO_3H$, —O—COOH, —O—[P(=O)(OH)$_2$], —O—[P(=O)(OH)], —$CH_2$—COOH; preferably each occurrence of A, if present, is independently selected from the group comprising H, —$SO_3H$, —COOH, —O—COOH, —$CH_2$—COOH; most preferably A is absent or occurrence of A, if present, is independently selected from the group comprising H, —COOH, —$CH_2$—COOH;

$X^-$ is selected from the group comprising $F^-$, $Cl^-$, $Br^-$, $I^-$, $ClO_4^-$, $BF_4^-$, $PF_6^-$, $AsF_6^-$, $SbF_6^-$, $NO_2^-$, $NO_3^-$, $HSO_4^-$, $SO_4^{2-}$, $PO_4^{3-}$, $HPO_4^{2-}$, $CF_3CO_2^-$, $CF_3CO_3^-$, $CO_3^{2-}$, $CF_3SO_3^-$, $C_1$-$C_6$ carboxylate, $CN^-$, $SCN^-$, $OCN^-$, $CNO^-$, $N_3^-$, tosylate, mesylate, trifluoromethanesulfonate, trifluoroethane sulfonate, di-trifluoromethanesulfonyl amino, docusate, xylenesulfonate; preferably $X^-$ is selected from the group comprising $F^-$, $Cl^-$, $HSO_4^-$, $SO_4^{2-}$, $PO_4^{3-}$, $HPO_4^{2-}$, $CF_3CO_2^-$, $CF_3CO_3^-$, $CF_3SO_3^-$; most preferably $X^-$ is selected from the group comprising $Cl^-$, $HSO_4^-$, $SO_4^{2-}$, $CF_3SO_3^-$.

In some embodiments of the ionic polymer of the present invention, the first monomer of formula I is

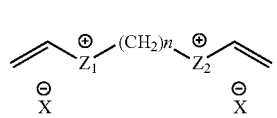

formula I

In some embodiments of the ionic polymer of the present invention, $Z_1$ and $Z_2$ are same (identical). In other embodiments, $Z_1$ and $Z_2$ are different.

In some embodiments of the ionic polymer of the present invention, when $Z_1$ and $Z_2$ is

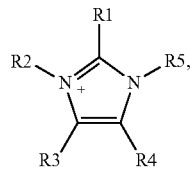

wherein R2 and R5 are bonds and R1, R3 and R4 are H, n is not 4.

In other embodiments of the ionic polymer of the present invention, when $Z_1$ and $Z_2$ is

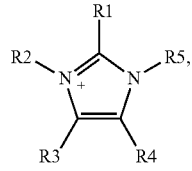

wherein R2 and R5 are bonds and n is 4, at least one of R1, R3 and R4 is not H.

In some preferred embodiments of the ionic polymer of the present invention, $C_1$-$C_6$ carboxylate are selected from the group comprising formate, acetate, propionate, butyrate, hexanoate, maleate, fumarate, oxalate, lactate, pyruvate.

The ratio between different monomers in the ionic polymers of the invention that comprises the first monomer and the second monomers can be any suitable ratio and may vary depending on the biomass to be processed. In some embodiments, the first and the second monomers are present in ratio 1:1.

According to some embodiments, the present invention provides monomers according to formula I selected from the group comprising

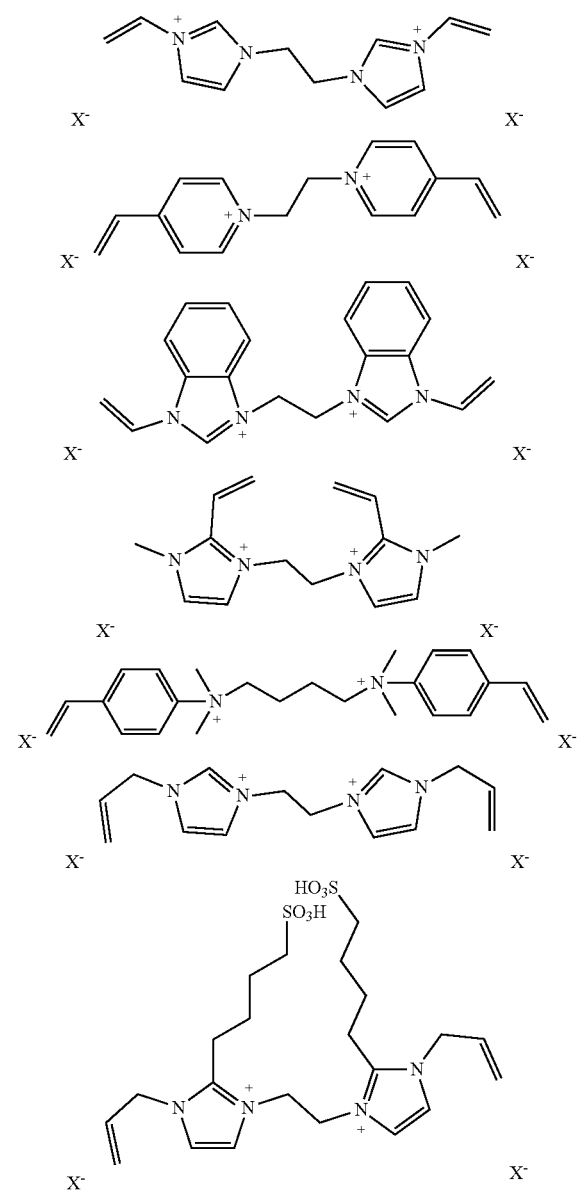

According to further embodiments, the present invention provides monomers according to formula I selected from the group comprising

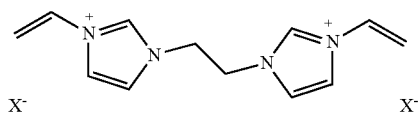

-continued

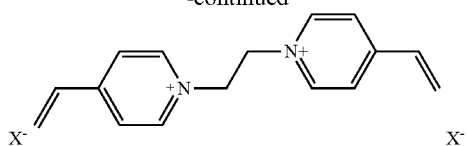

According to some embodiments, the present invention provides monomer according to formula II

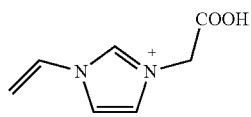

According to some embodiments, the present invention provides ionic polymers selected from the group comprising

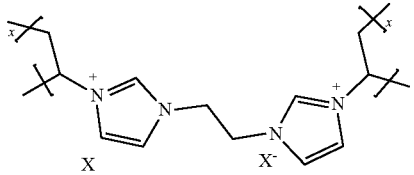

IP 1: X = Cl⁻
IP 2: X = CF₃SO₃⁻

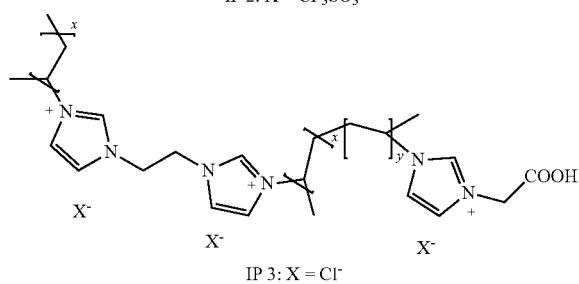

IP 3: X = Cl⁻

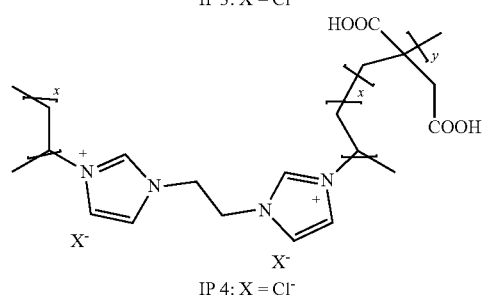

IP 4: X = Cl⁻

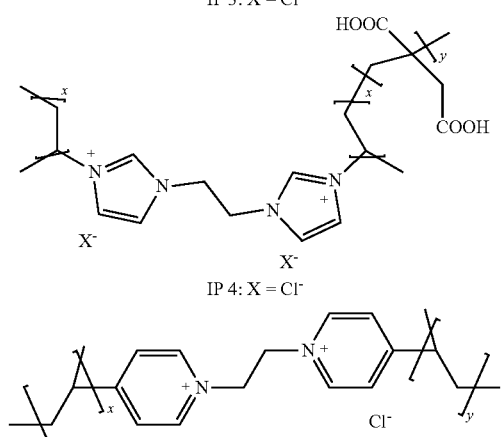

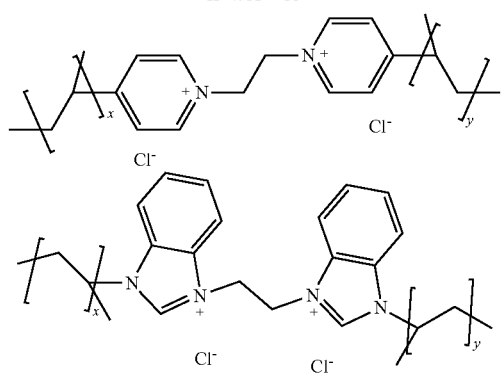

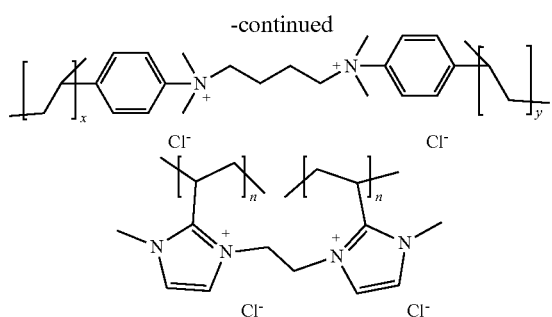

x and y are integers each independently selected within the range 1 to 1000; preferably 1 to 500 or 1 to 200; more preferably 1 to 100 or 1 to 50;

According to other embodiments, the present invention provides ionic polymers selected from the group comprising

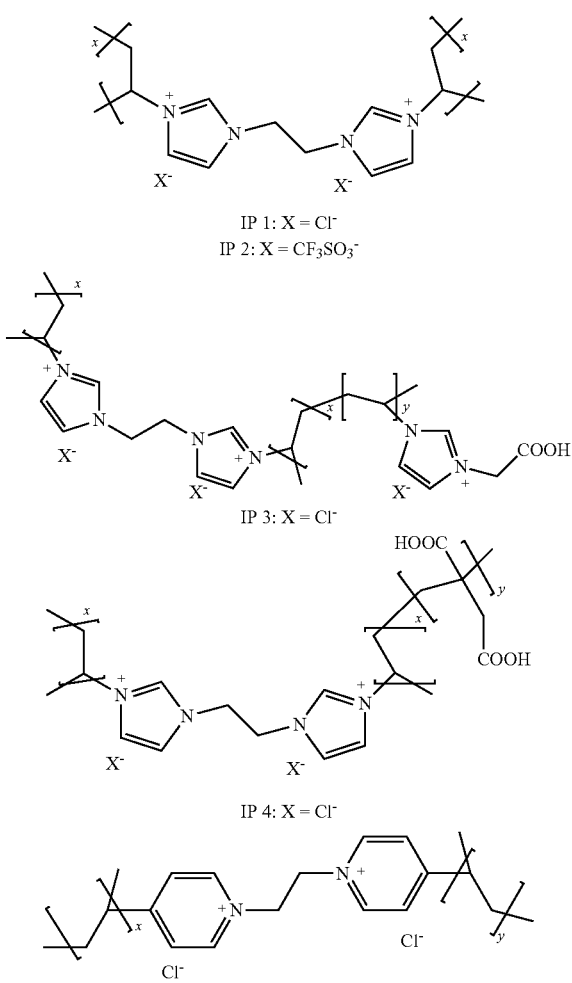

x and y are integers each independently selected within the range 1 to 1000; preferably 1 to 500 or 1 to 200; more preferably 1 to 100 or 1 to 50;

Ionic polymers (IPs) of the invention can be synthesized via several methods, including but not limited to the direct polymerization of appropriate ionic species, the chemical modification of non-IPs, etc. in different solvents (water, acetonitrile, alcohols (methanol, ethanol, propanol etc.), toluene, THF) (see Examples). Polymerization may include different approaches, e.g. free radical polymerization, living/controlling radical polymerization, reversible addition-fragmentation transfer, ionic and coordination polymerization. The anionic structure can be designed according to preference before or after polymerization. The resulting ionic polymer (IP) combines the general properties of the ionic monomer and the enabling properties of a solid catalyst due to the presence of acidic groups. In an embodiment of the invention, a salt is prepared with a cation and an anion, wherein both the cation and the anion contain styrene groups that can be polymerized using AIBN. It is essentially a very simple method and the ionic polymer is purified by removal of the excess AIBN by washing and filtration. In a specific embodiment of the invention, a salt that is composed of the 1-(1-vinylimidazolium)ethyl-3-vinylimdazolium] [dichloride]) is prepared. This salt, a pure compound, is then polymerized using the radical initiator AIBN. The ionic polymer is purified by removal of the excess AIBN by washing and filtration. As alternative to dichoride anion, a ditriflate anion can be obtained via anion exchange reaction prior polymerization.

The present invention also provides an ionic polymer network comprising cross-linked one or more ionic polymers of the invention.

In some embodiments, the ionic polymer network of the invention further comprises itaconic acid, citric acid and/or 1,4 butanediol.

In other embodiments, the ionic polymer network of the invention further comprises one or more metal catalysts. In some embodiments, the metal catalyst is a metal salt. In preferred embodiments anion in metal salt is selected from the group comprising $F^-$, $Cl^-$, $Br^-$, $I^-$, $ClO_4^-$, $BF_4^-$, $PF_6^-$, $AsF_6^-$, $SbF_6^-$, $NO_2^-$, $NO_3^-$, $HSO_4^-$, $SO_4^{2-}$, $PO_4^{3-}$, $HPO_4^{2-}$, $CF_3CO_2^-$, $CF_3CO_3^-$, $CO_3^{2-}$, $CF_3SO_3^-$, $C_1$-$C_6$ carboxylate, $CN^-$, $SCN^-$, $OCN^-$, $CNO^-$, $N_3^-$, tosylate, mesylate, trifluoromethanesulfonate, trifluoroethane sulfonate, di-trifluoromethanesulfonyl amino, docusate, xylenesulfonate salts, and metal ion is selected from the group comprising Na, Ba, Sr, Ca, Cd, Sn, Pb, Fe, Cu, Zn, Zr, Mn, Co, Ni, Li, Al, Cr, Mg, Mo, Hg, Ag, Au, Pt, Rh, Re, Ti, Pb, Bi, Ga, In, Sn, Ir, La, Hf, Ta, W, Os.

In some preferred embodiments, $C_1$-$C_6$ carboxylate are selected from the group comprising formate, acetate, propionate, butyrate, hexanoate, maleate, fumarate, oxalate, lactate, pyruvate.

The ionic polymer network of the invention comprising one or more metal catalysts provides better stability and reusability of the ionic polymer-metal combinations.

The preparation of the ionic polymer network of the invention with one or more metal catalysts typically consists in mixing or refluxing the ionic polymer network and metal salt in water/organic solvent overnight. See for example J. Am. Chem. Soc., 2012, 134, 11852-11855; Chem. Cat. Chem., 2016, 8, 2508-2515; J. Org. Chem., 2011, 76 (24), pp 10140-10147; Inorg. Chem., 2006, 45, 6396-6403.

The ionic polymers of the invention can be incorporated in membranes or attached to solid supports.

Another aspect of the invention provides membranes composed of ionic polymers of the invention. In some embodiments, the invention provides a polymer membrane comprising one or more ionic polymers of the invention. By adding appropriate copolymer (for example acrylic acid) to the salt used for preparation of ionic polymers of the invention and then polymerize the mixture it is possible to generate a polymer membrane. An approach for membrane formation is based on the template-free method via simple ionic complexations when an ionic monomer is copolymerized with appropriate organic acid/acid derivative (see Tauber K. et al, *Polym. Chem.,* 2015, 6, 4855-4858; Täuber K. et al, *ACS Macro Lett.,* 2015, 4(1), 39-42; Zhang S. et al, *Chem. Sci.,* 2015, 6, 3684-3691). As example, ionic monomer was dissolved in DMSO and stirred for 2 h at 60° C. The transparent solution was then poured onto a glass plate and the solvent was evaporated at 80° C. in an oven. The resulting non-porous dry polymer film was subsequently immersed into aqueous ammonia (0.2 wt %) overnight for pore formation and electrostatic complexation. The membrane was detached easily from the glass plate and washed several times with water.

Another aspect of the invention provides solid-supported ionic polymers. In some embodiments, the invention provides a solid support having at least one surface comprising one or more ionic polymers of the invention. Supported ionic polymers can be immobilized on different materials as a support: silicon or carbon (nanotube, wire) source, graphene or graphene oxide, zeolites, metal/metals alloys or metal/metal alloy oxides. As example, $FeO_x$ support has been oxidized in the oven in presence of oxygen at high temperature (500° C.) and its surface was modified with mixture of silanes dissolved in ethanol in presence of HCl afterwards. After drying at room temperature the support was uniformly impregnated with methanol solution of ionic polymer and AIBN. After drying at room temperature, the obtained material was placed in the oven at 95° C. for 2 h. By repeating the impregnation process the desire polymer loading might be achieved. Another example is stainless steel membrane comprising ionic polymers of the invention. A mixture containing ionic monomer (0.2-0.5, molar ratio), acrylic acid (0.1-0.6, molar ratio), and benzoin ethylether (1 wt %, as a photo-initiator) were dissolved in methanol to achieve a homogeneous solution, which was then dispersed by wettening onto stainless steel membrane and photo-crosslinked at room temperature by irradiation with UV light of 250 nm wavelength.

Ionic polymer attachment is also possible through surface grafting, which requires activation of the support by UV or $O_3$, $O_2$, $H_2$ or air plasmas. It involves the creation of reactive sites (radicals) on the polymer surface followed by the covalent linkage of a preformed polymer or, more commonly, by the polymerization of a monomer from those radical sites (see Alves P. et al, Colloids and Surfaces B: Biointerfaces, Volume 82, Issue 2, 1 Feb. 2011, 371-377; Barbey R. et al., *Chem. Rev.,* 2009, 109(11), 5437-5527). Another copolymer or polymerization initiator might also be used during the polymerisation process (as in case of membrane formation).

Another aspect of the invention provides use of ionic polymers of the invention or the combination thereof, membranes incorporating ionic polymers of the invention and/or solid-supported ionic polymers of the invention to produce fine chemicals (value added chemicals) from biomass. In preferred embodiments, the fine chemicals are lipids (for example fatty acids, mono- di- and tri-acylglycerides), sugars (for example monosaccharides, disaccharides, oligosaccharides), furanic compounds (for example furfural, 5-hydroxymethylfurfural (HMF) and HMF derivatives), humins, polyphenols and/or pectic compounds. In other embodiments, the fine chemicals are used as prebiotics.

Another aspect of the invention provides a method that involves the use of the ionic polymers of the invention or the combination thereof, membranes incorporating ionic polymers of the invention and/or solid-supported ionic polymers of the invention for producing fine chemicals (value added chemicals) from biomass. In preferred embodiments, the fine chemicals are lipids (for example fatty acids, mono- di- and tri-acylglycerides), sugars (for example monosaccharides, disaccharides, oligosaccharides), furanic compounds (for example furfural, 5-hydroxymethylfurfural (HMF) and HMF derivatives) humins, polyphenols and/or pectic compounds.

In the context of the present invention, lipids are preferably mono- di- and tri-acylglycerides or fatty acids, such as hexanedecenoic acid, palmitic acid, octanedecenoic acid and stearic acid.

In the context of the present invention, sugars refer to monosaccharides, disaccharides, or oligosaccharides. Monosaccharides include glucose, fructose and galactose, mannose, xylose and other C6 and C5 sugars. Disaccharides including sucrose, maltose, lactose and other possible combinations of monosaccharides. Oligosaccharides include longer chains of C6 and/or C5 sugars. In some embodiments, the sugars are one or more monosaccharides, one or more oligosaccharides, or a mixture thereof. In other embodiments, the sugars are two or more sugars that include at least one C5-C6 monosaccharide and at least one oligosaccharide. In yet other embodiments, the sugars are selected from glucose, galactose, fructose, xylose, and arabinose.

The sugars obtained by the methods of the present invention may be used as a food agent, for example, as a sweetening or flavouring agent, bulking agents or as substrates for fermentation and chemical conversion process. The sugars obtained by the methods of the present invention may be used for human and animal consumption or for non-human and non-animal consumption. In a preferred embodiment, the sugars obtained by the methods of the present invention are food grade sugars, suitable for human and animal consumption.

In the context of the present invention, furanic compounds are selected from the group consisting of furfural, 5-hydroxymethylfurfural (HMF) and derivatives of HMF likewise alkoxymethylfurfural, such as methoxymethylfurfural (MMF); and haloalkylfurfurals, such as 5-chloromethylfurfural. Also in the context of the present invention, furanic compounds can be obtained/derived from sugars that are obtained by methods of the present invention.

In the context of the present invention, humins can be obtained/derived from sugars that are obtained by methods of the present invention.

In the context of the present invention, polyphenols are phenolic acids or lignans (gallic acid, protocatechuic acid, vanillic acid, caffeic acid, syringic acid, p-coumaric acid, ferulic acid, sinapic acid) that are often bound to structural materials (carbohydrates) via C—O bond like in grains and seeds or exist in a free form like it fruits and vegetables. Hydrolysis using ionic polymers of the invention releases these phenolics from the biomass matrix, however they may still be bound to the sugar molecules or exist independently.

In the context of the present invention, pectin and pectic compound is typically made up of homogalacturonan (a-1, 4-linked galacturonic acid monomers) and rhamnogalacturonan (alternate galacturonic acid and rhamnose backbone with neutral side chains). Controlled hydrolysis of pectic containing agricultural by-products like sugar beet, apple, olive and citrus by ionic polymers of the invention can be used to produce oligo-galacturonides, galactooligosaccharides, rhamnogalacturonan-oligosaccharides, etc.

The sugars of certain DP and polyphenols obtained by the methods of the present invention can be used as prebiotics.

The DP can be controlled by the proper selection of IP and the process parameters (for example, DP 2-10 or DP 2-30).

In the context of the present invention, prebiotics are typically plant-derived polyphenols and carbohydrate compounds selected from the group comprising oligosaccharides, such as fructans and galactans, resistant starch, pectin, beta-glucans, mannans, arabinoxylans, and xylooligosaccharides or mixture of thereof. Fructans are a category of carbohydrate consisting of fructooligosaccharides (FOS) and inulins, while galactans consist of galactooligosaccharides (GOS). The fine chemicals (value added chemicals) obtained by the methods of the present invention can be used prebiotics.

The term "biomass," as used herein, refers to living or dead biological material that can be used in one or more of the disclosed methods and processes of the invention. Biomass can comprise any cellulosic, chitinous, oleaginous or lignocellulosic material and includes materials comprising cellulose, and optionally further comprising hemicellulose, lignin, starch, oligosaccharides and/or monosaccharides, biopolymers, natural derivatives of biopolymers, their mixtures, and breakdown products (e.g., metabolites). Biomass can also comprise additional components, such as salts, proteins and/or lipids. Biomass can be derived from a single source, or biomass can comprise a mixture derived from more than one source. Some specific examples of biomass include, but are not limited to, bioenergy crops, agricultural residues, agricultural and food process by-products, municipal solid/liquid waste, industrial solid/liquid waste, sludge from paper manufacture, yard waste, wood and forestry waste. Additional examples of biomass include, but are not limited to, corn grain, corn cobs, crop residues such as corn husks, corn stover, grasses, wheat, wheat straw, hay, rice straw, switchgrass, waste paper, sugar cane bagasse, sorghum, soy, components obtained from milling of grains, trees (e.g., pine), branches, roots, leaves, wood chips, wood pulp, sawdust, shrubs and bushes, vegetables, fruits, flowers, animal manure, multi-component feed, yeast cell walls and crustacean biomass (i.e., chitinous biomass). In a preferred embodiment, biomass is selected from the group comprising cellular biomass, food wastes/residues/side-streams, agricultural wastes, forestry wastes, timber wastes, processed wood, paper, pulp, algae, energy crops, fast-growing trees/plants, yeast cell walls. In another preferred embodiment, biomass is selected from the group consisting of cellulose, hemicelluloses, lignocelluloses and mixtures thereof.

According to some embodiments of the invention, it is possible to use a mixture of the ionic polymers of the invention in the uses of the inventions and in the methods of the invention. Ionic polymers mixture can be obtained either by physical mixing of each ionic polymer of the invention or by protonation reaction (last step in preparation) in a mixture of appropriate acids (for example HCl and $H_2SO_4$).

Essentially, the biomass is heated in the presence of one or more ionic polymers of the invention, membranes incorporating ionic polymers of the invention and/or solid-supported ionic polymers of the invention in water or organic solvent to obtain fine chemicals, such as lipids, sugars, furanic compounds, humins, polyphenols and/or pectic compounds depending on the type of biomass used, pretreatment steps of the biomass and the reaction conditions (time, temperatures, solvents and other reagents).

Another aspect of the invention provides a method for producing one or more fine chemicals selected from the group comprising lipids, sugars, furanic compounds, humins, polyphenols and/or pectic compounds from biomass, the method comprising the steps of:

a) providing biomass;
b) optionally determining lipids and/or sugars contents in the biomass;
c) optionally pretreating the biomass;
d) contacting the biomass with a catalyst to form a reaction mixture, wherein the catalyst is an ionic polymer of the invention or a combination of ionic polymers of the invention, the ionic polymer network of the invention, a solid-supported ionic polymers of the invention and/or a membrane incorporating ionic polymers of the invention;
e) degrading the biomass in the reaction mixture to produce a liquid phase and a solid phase, wherein the liquid phase includes the one or more fine chemicals, and the solid phase includes residual biomass;
f) isolating at least a portion of the liquid phase from the solid phase; and
g) recovering the one or more fine chemicals from the isolated liquid phase.

In one embodiment, the step d) contacting the biomass with a catalyst to form a reaction mixture consists in adding an appropriate water or organic solvent and an effective amount of the catalyst to the biomass to form a reaction mixture, wherein the catalyst is an ionic polymer of the invention or a combination of ionic polymers of the invention, the ionic polymer network of the invention, a membrane incorporating ionic polymers of the invention and/or a solid-supported ionic polymers of the invention; and degrading step e) consists in heating the reaction mixture of step d) during appropriate time and subsequently cooling to room temperature (typically 20-25° C.).

An embodiment of the invention provides a method for producing one or more fine chemicals selected from the group comprising lipids, sugars, furanic compounds, humins, polyphenols and/or pectic compounds from biomass, the method comprising the steps of:

a) providing biomass
b) optionally determining lipids and/or sugars contents in the biomass;
c) optionally pretreating biomass;
d) adding an appropriate water or organic solvent and an effective amount of a catalyst to the biomass to form a reaction mixture, wherein the catalyst is an ionic polymer of the invention or a combination of ionic polymers of the invention, the ionic polymer network of the invention, a solid-supported ionic polymers of the invention and/or a membrane incorporating ionic polymers of the invention;
e) heating the mixture of step d) during appropriate time;
f) cooling to room temperature;
g) recovering the one or more fine chemicals.

In some embodiments of the method of the present invention, the organic solvent is selected from the group comprising alcohol (such as methanol, ethanol, butanol, ethylene glycol, etc.), ether (such as dimethoxyethane, diglyme, butyl methyl ether, etc.), ketone (such as methyl isobutyl ketone, N-methyl-2-pyrrolidone, etc.), DMSO, DME, DMF, THF, ionic liquids.

In some embodiments, ionic liquids used as organic solvent in the methods of the invention comprise cation and anion moieties and are referred as green organic solvents as they are non-volatile and therefore can be easily contained. Cations present in ionic liquids of the invention are choline, imidazolium, pyrrolidinium, pyridinium, ammonium and phosphonium based cations and/or selected from the group comprising

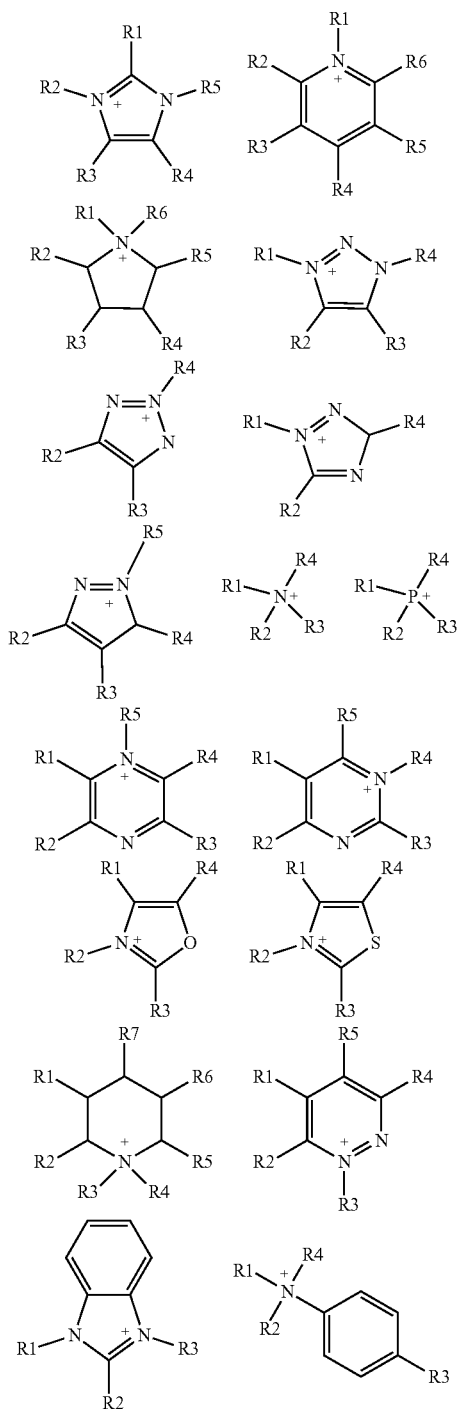

preferably selected from the group comprising:

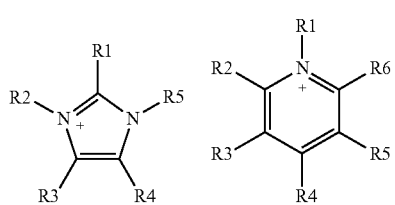

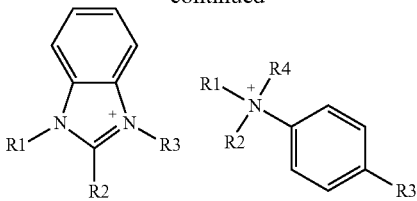

most preferably selected from the group comprising:

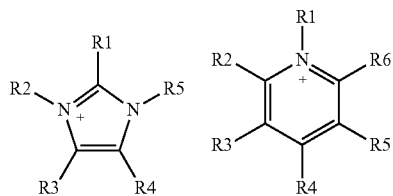

wherein R1, R2, R3, R4, R5, R6 and R7 are each independently selected from the group comprising a bond, H, $C_1$-$C_6$ alkyl, allyl, $CH_3$—$(CH_2)p$-O—$(CH_2)q$-$CH_3$, $C_1$-$C_6$ alkoxy, $C_1$-$C_6$ alkoxyalkyl, benzyl, —$SO_3H$, —$(CH_2)q$-$SO_3H$; preferably R1, R2, R3, R4, R5, R6 and R7 are each independently selected from the group comprising a bond, H, $C_1$-$C_6$ alkyl; most preferably R1, R2, R3, R4, R5, R6 and R7 are each independently selected from the group comprising a bond and H;

Anions present in the ionic liquids of the invention can be any suitable anion. In preferred embodiments, anion is selected from the group comprising $F^-$, $Cl^-$, $Br^-$, $I^-$, $ClO_4^-$, $BF_4^-$, $PF_6^-$, $AsF_6^-$, $SbF_6^-$, $NO_2^-$, $NO_3^-$, $HSO_4^-$, $SO_4^{2-}$, $PO_4^{3-}$, $HPO_4^{2-}$, $CF_3CO_2^-$, $CF_3CO_3^-$, $CO_3^{2-}$, $CF_3SO_3^-$, $C_1$-$C_6$ carboxylate, $CN^-$, $SCN^-$, $OCN^-$, $CNO^-$, $N_3^-$, tosylate, mesylate, trifluoromethanesulfonate, trifluoroethane sulfonate, di-trifluoromethanesulfonyl amino, docusate, xylenesulfonate; preferably anion is selected from the group comprising $F^-$, $Cl^-$, $HSO_4^-$, $SO_4^{2-}$, $PO_4^{3-}$, $HPO_4^{2-}$, $CF_3CO_2^-$, $CF_3CO_3^-$, $CF_3SO_3^-$; most preferably anion is selected from the group comprising $Cl^-$, $HSO_4^-$, $SO_4^{2-}$, $CF_3SO_3^-$.

In some embodiments of the methods of the present invention, recovering the one or more fine chemicals, such as lipids, sugars, furanic compounds, humins, polyphenols and/or pectic compounds can be done by any technic known in the art, such as filtration, centrifugation or gravity settling.

In the context of the present invention, decomposing or degrading biomass encompasses also transforming and hydrolysing biomass, extracting from biomass compounds or fine chemicals of interest, such as lipids, sugars, furanic compounds, humins, polyphenols and/or pectic compounds, or any other activity that allows decomposition, degradation, transformation of biomass into compounds or fine chemicals of interest.

Some embodiments of the invention provide methods of producing one or more sugars from various biomass using ionic polymers of the invention or a combination thereof, membranes incorporating ionic polymers of the invention and/or solid-supported ionic polymers of the invention to decompose or degrade biomass.

In some embodiments, the methods described herein using the ionic polymers of the invention or a combination thereof, membranes incorporating ionic polymers of the invention and/or solid-supported ionic polymers of the invention can hydrolyse the cellulose and/or hemicellulose into one or more sugars, including monosaccharides, disaccharides, and/or oligosaccharides.

An embodiment of the invention provides a method for producing one or more sugars from biomass, the method comprising the steps of:
a) providing biomass;
b) optionally determining sugars contents in the biomass;
c) optionally pretreating the biomass;
d) contacting the biomass with a catalyst to form a reaction mixture, wherein the catalyst is an ionic polymer of the invention or a combination of ionic polymers of the invention, the ionic polymer network of the invention, a solid-supported ionic polymers of the invention and/or a membrane incorporating ionic polymers of the invention;
e) degrading the biomass in the reaction mixture to produce a liquid phase and a solid phase, wherein the liquid phase includes one or more sugars, and the solid phase includes residual biomass;
f) isolating at least a portion of the liquid phase from the solid phase; and
g) recovering the one or more sugars from the isolated liquid phase.

In some embodiments, biomass can be subjected to a multi-step degradation, such as hydrolysis process. For example, in some embodiments, biomass containing C5 and C6 sugars can be first contacted with the ionic polymers of the invention or the combination thereof, membranes incorporating ionic polymers of the invention and/or solid-supported ionic polymers of the invention to recover only C5 oligomer sugars or C5 monomer sugars, that can further provide furfural if the reaction time is extended and then the residual material with the addition of appropriate solvent is further processed in a second degradation step (for example hydrolysis step) to recover C6 oligomer sugars and/or C6 monomer sugars, that can further provide 5-hydroxymethylfurfural (HMF) and derivatives thereof if the reaction time is extended. Temperature and reaction time of each step is individually set for optimizing extraction. Typically a multi-step process requires extended reaction time comparing to the one-step process. If the ionic polymer of the invention or the combination of ionic polymers of the invention is unsupported, then it stays in the first solid phase that includes residual material. If the ionic polymer of the invention or the combination of ionic polymers of the invention is supported it stays on the support. In any case, in this multi-step process it is not necessary to add or reintroduce again ionic polymers of the invention or the combination thereof. Thus another embodiment of the invention provides a method for producing C5 and C6 sugars, furfural, 5-hydroxymethylfurfural (HMF) and derivatives of HMF from biomass, the method comprising the steps of:
a) providing biomass;
b) optionally determining sugars contents in the biomass;
c) optionally pretreating the biomass;
d) contacting the biomass with a catalyst to form a reaction mixture, wherein the catalyst is an ionic polymer of the invention or a combination of ionic polymers of the invention, the ionic polymer network of the invention, a solid-supported ionic polymers of the invention and/or a membrane incorporating ionic polymers of the invention;
e) degrading the biomass in the reaction mixture to produce a first liquid phase and a first solid phase, wherein the first liquid phase includes C5 oligomer sugars and/or C5 monomer sugars and can further include furfural if the time of degrading step is extended, and the first solid phase includes residual material;
f) isolating at least a portion of the first liquid phase from the first solid phase;
g) recovering C5 oligomer sugars and/or C5 monomer sugars and/or furfural from the isolated first liquid phase;
h) contacting the first solid phase that includes residual material with the same catalyst as in step d) or with a different catalyst, to form a reaction mixture, wherein the catalyst is an ionic polymer of the invention or a combination of ionic polymers of the invention, the ionic polymer network of the invention, a solid-supported ionic polymers of the invention and/or a membrane incorporating ionic polymers of the invention;
i) further degrading the first solid phase that includes residual material in the reaction mixture to produce a second liquid phase and a second solid phase, wherein the second liquid phase includes C6 oligomer sugars and/or C6 monomer sugars and can further include 5-hydroxymethylfurfural (HMF) and derivatives of HMF and/or humins if the time of degrading step is extended, and the second solid phase includes residual material;
j) isolating at least a portion of the second liquid phase from the second solid phase; and
k) recovering C6 oligomer sugars and/or C6 monomer sugars and/or 5-hydroxymethylfurfural (HMF) and derivatives of HMF and/or humins from the isolated second liquid phase.

In some embodiments of the multi-step degradation method of the invention, it is understood that the catalyst in step h) can be already present in the process (in the first solid phase, in the membrane and/or supported) and therefore it is the same as in step d) of the method or it can be different, i.e. subsequently added.

In another embodiment of the invention, decomposition reactions of the biomass containing cellulose and hemicellulose can be allowed to continue towards the formation of other value-added chemicals such as 5-hydroxymethylfurfural (HMF) and its derivatives, furfural and humins. In this decomposition reaction, the reaction time is typically longer than the reaction time necessary for obtaining C5/C6 oligomer sugars and/or C5/C6 monomer sugars. HMF is a versatile platform chemical and a precursor to other platform and value added chemicals. Thus an embodiment of the invention provides a method for producing 5-hydroxymethylfurfural (HMF) or derivatives thereof, furfural and/or humins from biomass, the method comprising the steps of:
a) providing biomass;
b) optionally determining sugars contents in the biomass;
c) optionally pretreating the biomass;
d) contacting the biomass with a catalyst to form a reaction mixture, wherein the catalyst is an ionic polymer of the invention or a combination of ionic polymers of the invention, the ionic polymer network of the invention, a solid-supported ionic polymer of the invention and/or a membrane incorporating ionic polymers of the invention;
e) degrading the biomass in the reaction mixture to produce a liquid phase and a solid phase, wherein the liquid phase includes 5-hydroxymethylfurfural or derivatives thereof, furfural or humins, and the solid phase includes residual biomass;
f) isolating at least a portion of the liquid phase from the solid phase; and g) recovering 5-hydroxymethylfurfural or derivatives thereof, furfural or humins from the isolated liquid phase.

Optionally, prior to any use, sugars and/or lipids contents are determined in the biomass based on the standard methods. Lipids can be determined/extracted using Folch method (Folch J, Lees M, Stanley, GHS, 1957, 226, 497-509) involving a mixture of methanol, chloroform and water (2:1:0.8, v/v/v), and phase separation afterwards. Determination of sugars is performed according, for example, NREL protocol for "Determination of Structural Carbohydrates and Lignin in Biomass". For example, 1 ml of 72% sulfuric acid was added to 100 mg of biomass. The slurry was stirred for 1 h at 30° C., followed by addition of 28 ml of deionized water. Mixture was autoclaved at 120 C for 1 h, cooled to room temperature and was used for sugar analysis by HPLC and acid-soluble lignin determination using UV-spectrophotometry at 205 nm wavelength. The same hydrolysate was used for proteins analysis according the Bradford protein assay. The residue from acid hydrolysis was washed with 100 mL of water and then dried at 105° C. to determine Klason lignin.

The optional pretreatment of the biomass, used in the methods described herein, uses one or more methods selected from the group consisting of washing, solvent-extraction, solvent-swelling, comminution, milling, steam pretreatment, explosive steam pretreatment, dilute acid pretreatment, hot water pretreatment, alkaline pretreatment, lime pretreatment, wet oxidation, wet explosion, ammonia fiber explosion, organosolvent pretreatment, biological pretreatment, ammonia percolation, ultrasound, electroporation, microwave, supercritical $CO_2$, supercritical $H_2O$, ozone, and gamma irradiation. The optional pretreatment of the biomass includes for example the milling of the biomass. To overcome the obstacle of the reaction rate being limited by the surface reaction and mass transfer, a pretreatment processes of the biomass via ball milling, which leads to a reduction in crystallinity and an increase in the specific surface area of cellulosic material, is highly recommended. Depending on performed mechanical ball milling of biomass there is a decrease in structural particle size, reduction of the degree of polymerization of cellulose, and an increase in the amorphous content of cellulose.

The effective amount of the ionic polymers of the invention or a combination thereof used in the methods described herein can depend on several factors including, for example, the type of biomass, the amount of the biomass, the content of the sugars and/or lipids in the biomass, the type and number of pretreatment(s) applied to the biomass, and the reaction conditions (such as temperature and time). An effective amount of the ionic polymer of the invention refers to an amount sufficient to degrade biomass to, for instance, attain one or more desired sugars, lipids or other fine chemicals and value-added chemicals (such as 5-hydroxymethylfurfural (HMF) or its derivatives, furfural and humins). In some embodiments, the effective amount of the ionic polymer of the invention is usually 0.05:1 w/w to 10:1 w/w, 0.5:1 w/w to 10:1 w/w, 1:1 w/w to 1:5 w/w, preferably 0.1:1 w/w to 1:5 w/w compared to sugars content in the biomass.

The ratio biomass to water used in the methods described herein can depend on several factors, including for example the type of biomass and the amount of biomass. In some embodiments, the ratio biomass to water or organic solvent (such as alcohol, ether, ketone, DMSO, DME, DMF) used in the methods described herein is ranging from 1:100 w/v to 1:1 w/v, preferably 1:50 w/v to 1:10 w/v.

The preferred temperature profile for the heating used in the methods described herein depends on the biomass starting material being used and also the intended monomer and oligomer mixture being produced. The heating temperature should preferably be held at a maximum of 250° C., in some embodiments at a maximum of 200° C. In some embodiments, the heating temperature is between 100° C. and 250° C., or between 100° C. and 200° C. preferably between 120° C. to 220° C. or between 120° C. to 220° C. Preferably, for small-scale applications, the heating is done in a high-pressure autoclave reactor, which after sealing, is heated for appropriate reaction time and temperature.

In some embodiments, the appropriate reaction time in the methods described herein is for example between 10 minutes and 10 hours, preferably between 0.5 hour and 5 hours or between 1 hour and 3 hours, depending on the type and amount of biomass.

In some embodiments, the methods for producing one or more, sugars, furanic compounds, humins, polyphenols and/or pectic compounds from biomass using the ionic polymers of the invention or a combination thereof, a membrane incorporating ionic polymers of the invention and/or a solid-supported ionic polymers of the invention, further include recovering the sugars, the furanic compounds, humins, polyphenols and/or pectic compounds that are produced from the hydrolysis of biomass. The sugars and the furanic compounds, which are typically soluble, can be separated from the insoluble residual biomass using technology well known in the art such as, for example, centrifugation, filtration, and gravity settling.

Recovering of the sugars, the furanic compounds, humins, polyphenols and/or pectic compounds can be performed in the hydrolysis reactor or in a separator vessel. In an exemplary embodiment, the method for producing one or more sugars, furanic compounds, humins, polyphenols and/or pectic compounds from biomass is performed in a system with a hydrolysis reactor and a separator vessel. Reactor effluent containing the monosaccharides, disaccharides, oligosaccharides, furanic compounds, humins, polyphenols and/or pectic compounds is transferred into a separator vessel and is washed with a solvent (for example water), by adding the solvent into the separator vessel and then separating the solvent in a continuous centrifuge. Alternatively, in another exemplary embodiment, a reactor effluent containing residual solids (for example residual biomass) is removed from the reactor vessel and washed, for example, by conveying the solids on a porous base (for example a mesh belt) through a solvent (for example water) wash stream. Following contact of the stream with the reacted solids, a liquid phase containing the monosaccharides, disaccharides, oligosaccharides, furanic compounds, humins, polyphenols and/or pectic compounds is generated. Optionally, residual solids can be separated by a cyclone. Suitable types of cyclones used for the separation can include, for example, tangential cyclones, spark and rotary separators, and axial and multi-cyclone units.

In another embodiment, recovering of the sugars, the furanic compounds, humins, polyphenols and/or pectic compounds is performed by batch or continuous differential sedimentation. Reactor effluent is transferred to a separation vessel, optionally combined with water and/or enzymes for further treatment of the effluent. Over a period of time, solid biomaterials (for example residual treated biomass), the catalyst (for example the ionic polymer of the invention), and the sugar-containing aqueous material, the furanic-containing aqueous material and/or humins-containing aqueous material, polyphenols-containing aqueous material and/or pectic compounds-containing aqueous material can be separated by differential sedimentation into a plurality of phases (or layers). Generally, the catalyst layer can sediment to the bottom, and depending on the density of the residual biomass, the biomass phase can be on top of, or below, the aqueous phase. When the phase separation is performed in a batch mode, the phases are sequentially removed, either from the top of the vessel or an outlet at the bottom of the vessel. When the phase separation is performed in a continuous mode, the separation vessel contains one or more than one outlet means (for example two, three, four, or more than four), generally located at different vertical planes on a lateral wall of the separation vessel, such that one, two, or three phases are removed from the vessel. The removed phases are transferred to subsequent vessels or other storage means. By these processes, one of skill in the art would be able to capture (1) the catalyst layer and the aqueous layer or biomass layer separately, or (2) the catalyst, aqueous, and biomass layers separately, allowing efficient catalyst recycling, retreatment of biomass, and separation of sugars. Moreover, controlling rate of phase removal and other parameters allows for increased efficiency of catalyst recovery. Subsequent to removal of each of the separated phases, the catalyst and/or biomass can be separately washed by the aqueous layer to remove adhered sugars, furanic compounds, humins, polyphenols and/or pectic compounds.

In some embodiments, the sugars, the furanic compounds, humins, polyphenols and/or pectic compounds isolated from the vessel can be subjected to further processing steps (for example as in drying, fermentation) to produce biofuels and other bio-products.

The residual biomass isolated from the vessels can be useful as a combustion fuel, as fertilizer or as a feed source of non-human animals such as livestock or to a subsequent step for additional post-processing.

Another aspect of the invention provides a method that involves the use of the ionic polymers of the invention or a combination thereof, a membrane incorporating ionic polymers of the invention and/or a solid-supported ionic polymers of the invention for selectively converting polysaccharide polymers with a high degree of polymerization (DP) into mono- and oligosaccharides with a specific and/or lower degree of polymerization. For example, under optimized conditions it is possible to isolate only glucose/fructose or sugar oligomers with variable degree of polymerization (DP 2-DP 12).

Another aspect of the invention provides a method that involves the use of the ionic polymers of the invention or a combination thereof, a membrane incorporating ionic polymers of the invention and/or a solid-supported ionic polymers of the invention for extraction of lipids, such as fatty lipids, from biomass, wherein additional catalysts and/or additional gases ($CO_2$, $H_2$ etc.) are also used. For example, continuous extraction of the product or products may be employed, e.g. using an appropriate solvent or gas. As examples, supercritical $CO_2$ can be used in combination with the ionic polymer of the invention to extract lipids, leaving the remaining material to undergo transformation. If a catalyst such as Rh, Pt, Pd, their complex, salt or metal oxide, etc. is introduced to the reaction system in presence of $H_2$, the released sugars can be converted into alkanes.

The ionic polymers of the invention or a combination thereof, a membrane incorporating ionic polymers of the invention and/or a solid-supported ionic polymers of the invention can be used for extraction of lipids from biomass according to the methods known in the art (see Young, G. et al., Separation and Purification Technology 72, 118-121 (2010); Choi, S.-A. et al., Algal Research, 3, 44-48 (2014); Kim, Y.-H. et al., Bioresource Technology 109, 312-315 (2012); Sahena, F. et al., A review. Journal of Food Engineering 95, 240-253 (2009)).

The methods of the present invention can be used in diverse chemical, biotechnological and other industrial and non-industrial applications for transforming biomass to fine chemicals, simple constituents and subsequent derivatives and commodities.

The fine chemicals obtained by the methods of the present invention, such as polysaccharides and derivatives thereof, oligosaccharides and derivatives thereof and polyphenols and polyphenol extracts, can be used in cosmetic compositions and/or in preparation thereof. Indeed, in some embodiments cosmetic compositions are based on plant extracts or microorganism extracts, such as polysaccharides and derivatives thereof, oligosaccharides and derivatives thereof and polyphenols and polyphenol extracts, obtained by the methods of the present invention. Derivatives of oligosaccharides are selected from the group comprising galacto-oligosaccharides, xylo-oligosaccharides, arabinoxylo-oligosaccharides, oligogalacturonides, b-glucan.

The fine chemicals obtained by the methods of the present invention, such as polysaccharides and derivatives thereof, oligosaccharides and derivatives thereof and polyphenols and polyphenol extracts, can be further used in cosmetic compositions for various cosmetic treatments of skin, and/or in methods for preventing or treating skin disorders, and/or for skin health promotion. Derivatives of oligosaccharides are selected from the group comprising galacto-oligosaccharides, xylo-oligosaccharides, arabinoxylo-oligosaccharides, oligogalacturonides, b-glucan.

The fine chemicals obtained by the methods of the present invention, such as polysaccharides and derivatives thereof, oligosaccharides and derivatives thereof and polyphenols and polyphenol extracts, can be further used as compounds having antioxidant activity, anti-wrinkle activity, anti-ultraviolet light activity, wound healing activity, and moisturizing effect.

The ionic polymers of the invention or a combination thereof and the methods of the invention have several advantages compared to the polymeric compound and methods of the prior art. For example, no ionic polymer leaching was observed. This allows the ionic polymers of the invention to be used for the biomass treatment and the recovered sugars to be considered as a food grade product. Further, the ionic polymer of the invention operates in water; there is no need for ionic liquid solvents and in some cases any other organic solvent. Since other polymeric compounds of the prior art operate in ionic liquids (ILs), separation of products is more complicated. Using the ionic polymers and the methods of the invention, the products are in water and can be easily separated by filtration. Also, the reaction is performed in water and altering the reaction conditions result in product variations with different degree of polymerization. Generally, reaction is taking place within a short reaction time. The method of the invention operates at moderate temperatures, typically less than 150° C., whereas the prior art methods needs temperatures of more than 150° C. In addition, the ionic polymers and the methods of the invention provide fewer by-products, which allows easier recovery of the desired products.

An important advantage of the ionic polymers of the invention or a combination thereof, membranes incorporating ionic polymers of the invention and/or solid-supported ionic polymers of the invention and use thereof for biomass hydrolysis, decomposition or degradation is their use in one-pot systems for decomposition and selective extracting the aforementioned useful fine chemicals (value added chemicals) from the biomass.

Due to recyclability, efficiency in production, avoidance of producing non-prebiotic ingredients such as sugar monomers, the ionic polymers of the invention or a combination thereof are novel and superior approach when it comes to production of prebiotics as well as biomass processing technology.

Those skilled in the art will appreciate that the invention described herein is susceptible to variations and modifications other than those specifically described. It is to be understood that the invention includes all such variations and modifications without departing from the spirit or essential characteristics thereof. The invention also includes all of the steps, features, compositions and compounds referred to or indicated in this specification, individually or collectively, and any and all combinations or any two or more of said steps or features. The present disclosure is therefore to be considered as in all aspects illustrated and not restrictive, the scope of the invention being indicated by the appended claims, and all changes which come within the meaning and range of equivalency are intended to be embraced therein.

The foregoing description will be more fully understood with reference to the following Examples. Such Examples, are, however, exemplary of methods of practising the present invention and are not intended to limit the application and the scope of the invention.

EXAMPLES

Preparation of Ionic Polymers

A generalized scheme of the ionic polymer IP 1 (poly[1-(1-vinylimidazolium)ethyl-3-vinylimdazolium] [dichloride]) (poly-[vimevim][2Cl]) and IP 2 (poly[1-(1-vinylimidazolium)ethyl-3-vinylimdazolium] [ditriflate]) (poly-[vimevim][2CF$_3$SO$_3$]) preparation is shown in Figure and the details for each step are provided below.

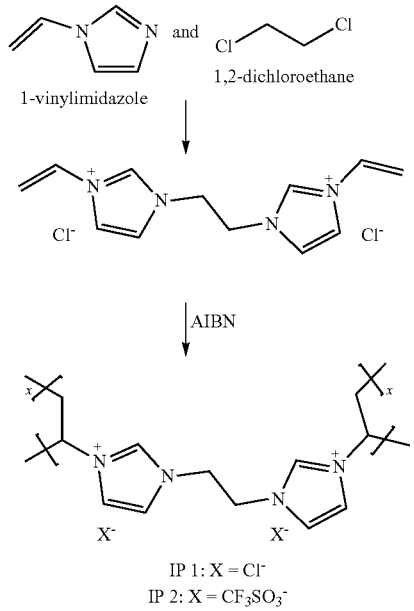

IP 1: X = Cl$^-$
IP 2: X = CF$_3$SO$_3^-$

Preparation of the Monomer [vimevim][2Cl]

A mixture of 1-vinylimidazole (0.2 mol) and 1,2-dichloroethane (0.1 mol) in acetonitrile (100 mL) was heated under reflux for 24 h. The product was precipitated with extra addition of acetonitrile and filtered afterwards. The collected solid was washed with diethyl ether/acetonitrile mixture (1:1, 3×15 mL) and dried under vacuum for 24 h.

Preparation of the Polymer poly-[vimevim][Cl]

Monomer [vimevim][2Cl] (1 g) was refluxed in 25 ml of methanol/propanol/toluene/acetonitrile (1:1:1:1) mixture in presence of azobisisobutyronitrile (AIBN) (0.5 wt %) overnight, filtered, washed with diethyl ether and dried overnight.

Preparation of the Monomer[vimevim][2CF$_3$SO$_3$]

Monomer [vimevim][2Cl] (5 g) and KCF$_3$SO$_3$ (6.5 g) were mixed together in 20 ml H$_2$O for 4 hours. Afterwards, the precipitated solid was collected and subjected to polymerization as above.

Preparation of the Monomer [vimevpyr][BrCl]

A mixture of 1-vinylimidazole (0.1 mol) and 1-bromo-2-chloroethane (0.13 mol) was stirred under Na at room temperature overnight. Afterwards, the isolated solid product was added to 2-vinylpyridine (0.1 mol) and acetonitrile (100 mL) and heated under reflux for 24 h. The obtained product was filtered and the collected solid was washed with diethyl ether/acetonitrile mixture (1:1, 3×15 mL) and dried under vacuum for 24 h. Similar approach can be used for any synthesis of monomer combining two different cations. Linker molecule (1-bromo-2-chloroethane as in the case above) can be changed according the preferences.

Preparation of the Monomer [vimSO$_3^-$evimSO$_3^-$]

A mixture of monomer [vimevim][2Cl] (0.1 mol), NH (0.2 mol) and propane sultone (0.2 mol) was refluxed in presence of THF (100 ml) under N$_2$ overnight. The obtained product was washed with THF (200 ml), filtered and the liquid phase was dried on the rotar yap.

Preparation of the Monomer [vimprCOOHvim][2Cl]

A mixture of 1-vinylimidazole (0.2 mol) and 3,3'-dichloropivalic acid (0.1 mol) in acetonitrile (100 mL) was heated under reflux for 24 h. The product was precipitated with extra addition of ethyl acetate and filtered afterwards. The collected solid was washed with diethyl ether/ethyl acetate mixture (1:1, 3×15 mL) and dried under vacuum for 24 h.

Preparation of the Monomer [vtrprOHvtr][2Cl]

A mixture of N-vinyltriazole (0.2 mol) and 1,3-dichloro-2-propanol (0.1 mol) in acetonitrile (100 mL) was heated under reflux for 24 h. The product was precipitated with extra addition of ethyl acetate and filtered afterwards. The collected solid was washed with diethyl ether/ethyl acetate mixture (1:1, 3×15 mL) and dried under vacuum for 24 h.

A generalized scheme of the ionic polymer IP 3 (poly[1-(1-vinylimidazolium)ethyl-3-vinylimdazolium] [dichloride]-co-3-carboxymethyl-1-vinylimidazolium] [chloride])

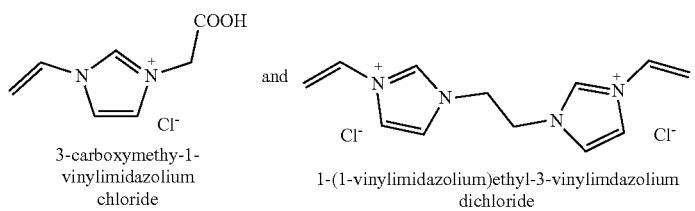

3-carboxymethy-1-vinylimidazolium chloride   and   1-(1-vinylimidazolium)ethyl-3-vinylimdazolium dichloride

|AIBN

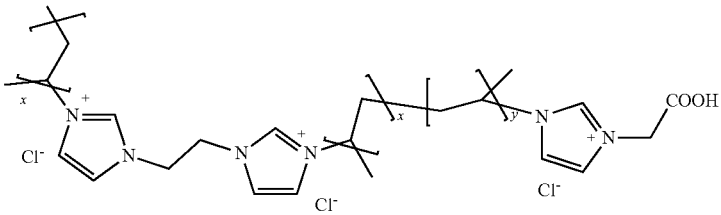

Preparation of Ionic Polymer Network with Itaconic Acid—IP 4

A mixture of monomer of IP 1 (0.017 mol) and itaconic acid (0.034 mol) in toluene/acetonitrile (50/50 mL) was heated under reflux for 24 h. The obtained solid product was filtered and washed with diethyl ether/acetonitrile mixture (1:1, 3×15 mL) and dried under vacuum for 24 h.

Preparation of Ionic Polymer Network with Citric Acid and 1,4-butanediol—IP 5

A mixture of monomer of IP 1 (0.017 mol), 1,4-butanediol (0.017 mol) and citric acid (0.017 mol) in toluene/acetonitrile (50/50 mL) was heated under reflux for 24 h. The obtained solid product was filtered and washed with diethyl ether/acetonitrile mixture (1:1, 3×15 mL) and dried under vacuum for 24 h.

Preparation of the monomer [1,1'-(1,2-ethanediyl)bis[4-vinylpyridinium]] [dichloride]

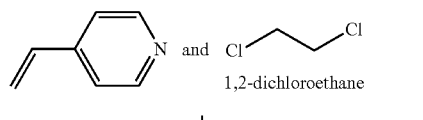

1,2-dichloroethane

↓

-continued

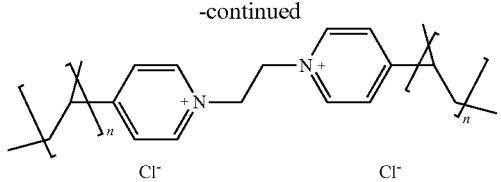

A mixture of 4-vinylpyridine (0.2 mol) and 1,2-dichloroethane (0.1 mol) in acetonitrile (100 mL) was heated under reflux for 24 h. The product was precipitated with extra addition of acetonitrile and filtered afterwards. The collected solid was washed with diethyl ether/acetonitrile mixture (1:1, 3×15 mL) and dried under vacuum for 24 h.

Preparation of the Polymer poly([1,1'-(1,2-ethanediyl)bis[4-vinylpyridinium]] [dichloride])

Monomer (10 g) was refluxed in 100 ml of methanol/propanol/toluene/acetonitrile (1:1:1:1) mixture in presence of azobisisobutyronitrile (AIBN) (0.5 wt %) overnight, filtered, washed with diethyl ether and dried overnight.

Preparation of the Monomer [3,3'-(1,2-ethanediyl)bis[1-vinylbenzimidazolium]] [dichloride]

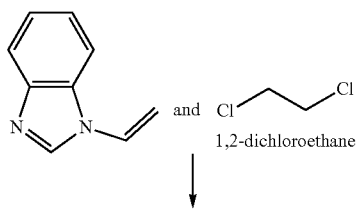

1,2-dichloroethane

↓

-continued

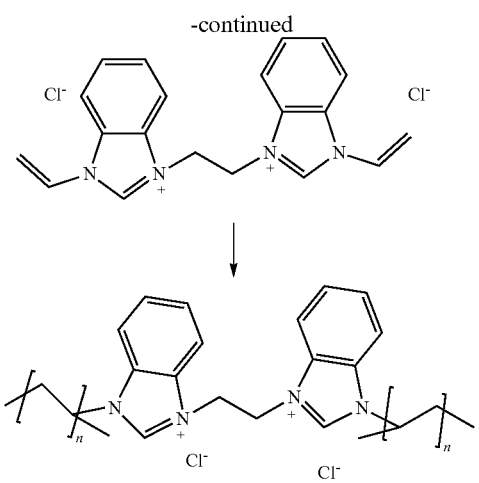

A mixture of 1-vinylbenzimidazole (0.2 mol) and 1,4-dichloroethane (0.1 mol) in acetonitrile (100 mL) was heated under reflux for 24 h. The product was precipitated with extra addition of acetonitrile and filtered afterwards. The collected solid was washed with diethyl ether/acetonitrile mixture (1:1, 3×15 mL) and dried under vacuum for 24 h.

Preparation of the Polymer poly([3,3'-(1,2-ethanediyl)bis[1-vinylbenzimidazolium]] [dichloride])

Monomer (10 g) was refluxed in 100 ml of methanol/propanol/toluene/acetonitrile (1:1:1:1) mixture in presence of azobisisobutyronitrile (AIBN) (0.5 wt %) overnight, filtered, washed with diethyl ether and dried overnight.

Preparation of the Monomer [3,3'-(1,2-ethanediyl)bis[1-methyl-2-vinylimidazolium]][dichloride]

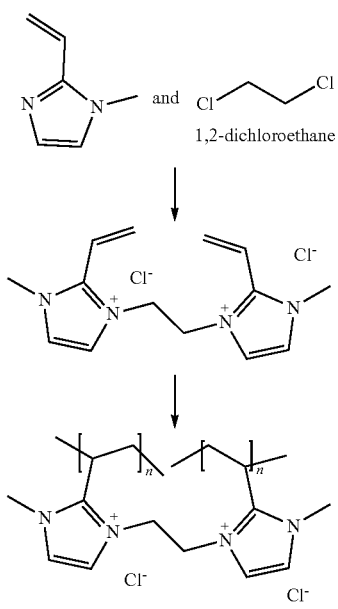

A mixture of 1-methyl-2-vinylimidazole (0.2 mol) and 1,4-dichloroethane (0.1 mol) in acetonitrile (100 mL) was heated under reflux for 24 h. The product was precipitated with extra addition of acetonitrile and filtered afterwards. The collected solid was washed with diethyl ether/acetonitrile mixture (1:1, 3×15 mL) and dried under vacuum for 24 h.

Preparation of the Polymer poly([3,3'-(1,2-ethanediyl)bis[1-methyl-2-vinylimidazolium] [dichloride])

Monomer (10 g) was refluxed in 100 ml of methanol/propanol/toluene/acetonitrile (1:1:1:1) mixture in presence of azobisisobutyronitrile (AIBN) (0.5 wt %) overnight, filtered, washed with diethyl ether and dried overnight.

Preparation of the Monomer tetramethylenebis[dimethylvinylbenzyl ammonium] [dichloride]

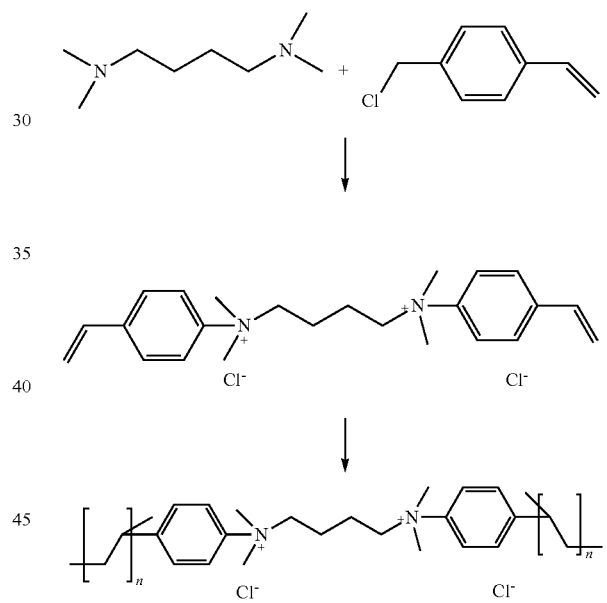

A mixture of 1,1,4,4-tetramethylbutanediamine (0.1 mol) and 4-chloromethylvinylbenzene (0.2 mol) in acetonitrile (100 mL) was heated under reflux for 24 h. The product was precipitated with extra addition of acetonitrile and filtered afterwards. The collected solid was washed with diethyl ether/acetonitrile mixture (1:1, 3×15 mL) and dried under vacuum for 24 h.

Preparation of the Polymer poly(tetramethylenebis[dimethylvinylbenzyl ammonium] [dichloride]

Monomer (1 g) was refluxed in 25 ml of methanol/propanol/toluene/acetonitrile (1:1:1:1) mixture in presence of azobisisobutyronitrile (AIBN) (0.5 wt %) overnight, filtered, washed with diethyl ether and dried overnight.

Preparation of the monomer 3,3'-[2-(oxiran-2-yl)ethyl]-1,2-ethanediyl]bis[1-allylimidazolium]] [dichloride]

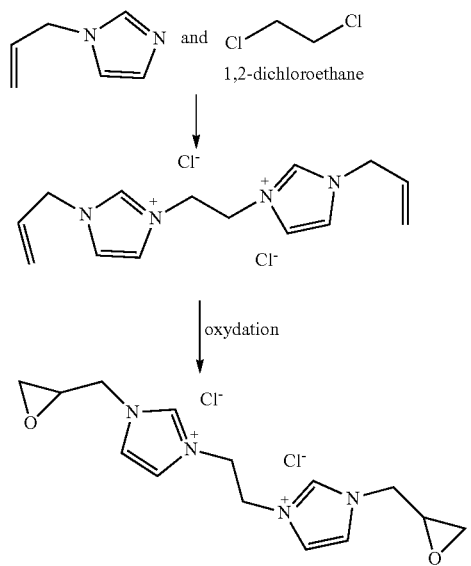

A mixture of 1-allylimidazole (0.2 mol) and 1,2-dichloroethane (0.1 mol) in acetonitrile (100 mL) was heated under reflux for 24 h. The product was precipitated with extra addition of acetonitrile and filtered afterwards. The collected solid was washed with diethyl ether/acetonitrile mixture (1:1, 3×15 mL) and dried under vacuum for 24 h. The obtained solid was oxidized using meta-chloroperoxybenzoic acid (0.2 mol) in presence of dichloromethane (50 ml) for 24 h. The obtained oily product was dried on rotarvap, washed with diethyl ether (150 ml) and dried under vacuum.

Preparation of the Polymer (3,3'-[2-(oxiran-2-yl)ethyl]-1,2-ethanediyl]bis[1-allylimidazolium]] [dichloride]-co-tris(2-aminoethyl)amine)

Monomer was refluxed with tris(2-aminoethyl)amine (1:1) in presence of iso-propanol for 24 h. The obtained product was washed with diethyl ether and dried under vacuum.

Preparation of 3,3'-(1,2-ethyl)bis[2-sulfobutyl-1-(2-propen-1-yl)]-imidazolium dichloride

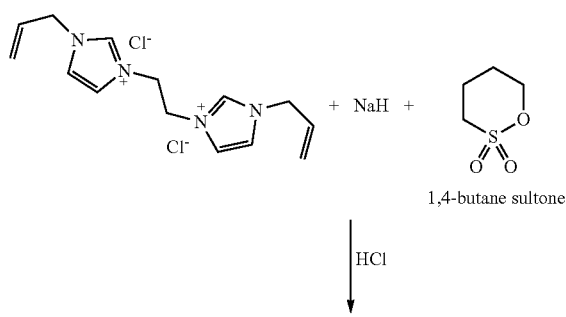

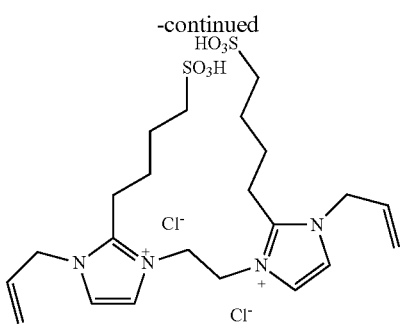

3,3'-(1,2-ethanediyl)bis[1-(2-propen-1-yl)-imidazolium dichloride (0.1 mol) was reacted with NaH (0.2 mol) and 1,4-butane sultone (0.2 mol) in THF (250 ml) for 24 h at room temperature. The obtained product was washed with THF/diethyl ether (100/100 ml) and protonated with HCL.

Comparison with the Prior Art US20160032038A1

Example 40 of US20160032038A1 "Preparation of poly(styrene-co-(1-vinyl-1H-imidazole)-co-divinylbenzene)" resulted a product that after extensive washing still had the presence of initial components (see FIG. 1).

Example 70 of US20160032038A1 "Preparation of poly(butyl-vinylimidazolium chloride-co-butylimidazolium chloride-co-styrene)": at the end of the reaction instead of the solid polymer there is a paste formed that doesn't resemble the description.

In addition, in the Example B5 of US20160032038A1 the authors state the loss of acidic activity, which represents the instability of the catalyst and leaching process during the catalysis.

Figure 2:
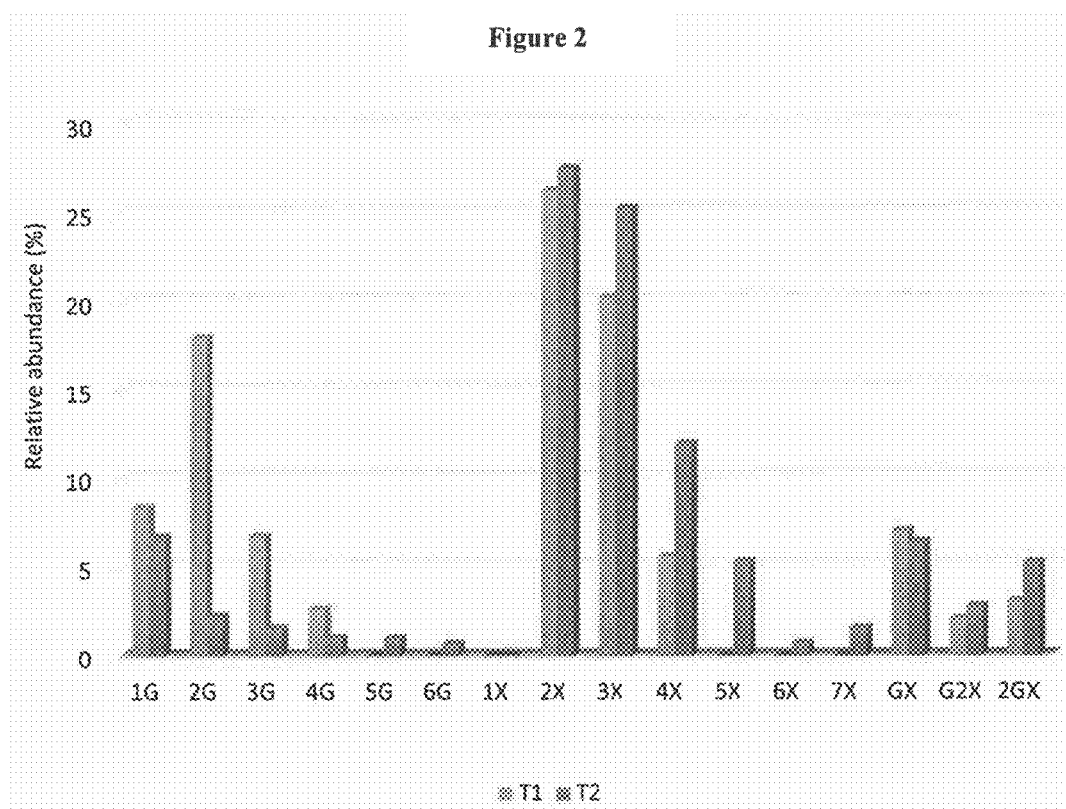
FIG. 2 shows oligomers distribution obtained from corn cob after the reaction with IP 1. G-glucose monomer, X-xylose monomer; number before G or X corresponds to the number of monomers in the chain, $T_1=135°$ C., $T_2=155°$ C., after 4 hours reaction.

Corncob Transformations into Mono and Oligosaccharides 20 g of corn cob were mixed with 1.75 g of IP 1 and 150 ml of $H_2O$ for 4 hours at appropriate temperature. After reaction, the mixture was cooled to room temperature, diluted with water and filtered for further analysis. The mono and oligosaccharides (50 and 70% yield) with the oligomers distribution are shown in FIG. 2.

Spent Coffee Grounds (SCG) Decomposition (Specific Low Degree of Polymerization (DP))

500 mg SCG, 20 mg of the ionic polymer poly[1-(1-vinylimidazolium)ethyl-3-vinylimdazolium] [dichloride]-co-3-carboxypropyl-1-vinylimidazolium] [chloride] and 10 ml of $H_2O$ were placed in a reactor, sealed and the reaction mixture was then heated at 200° C. for 30 min. After reaction the mixture was cooled to room temperature, diluted with water (50 ml) and filtered for further analysis. The obtained products (% per 100 mg of initial coffee loading):

| | |
|---|---|
| Monosaccharides | 3.12% |
| Disaccharides | 3.45% |
| Trisaccharides | 2.30% |
| HMF | 1% |

500 mg SCG, 100 mg of the ionic polymer IP 3 and 10 ml of $H_2O$ were placed in a reactor, sealed and the reaction mixture was then heated at 200° C. for 30 min. After reaction the mixture was cooled to room temperature, diluted with water (50 ml) and filtered for further analysis. The obtained products (% per 100 mg of initial coffee loading):

| | |
|---|---|
| Monosaccharides | 8.17% |
| Disaccharides | 3.14% |
| Trisaccharides | 0.00% |
| HMF | 1.7% |

500 mg SCG, 150 mg of the ionic polymer IP 4 and 10 ml of H₂O were placed in a reactor, sealed and the reaction mixture was then heated at 195° C. for 1 hour. After reaction the mixture was cooled to room temperature, diluted with water (50 ml) and filtered for further analysis. The obtained products (% per 100 mg of initial coffee loading):

| | |
|---|---|
| Monosaccharides | 3.17% |
| Disaccharides | 3.14% |
| Trisaccharides | 1.05% |
| HMF | 1.6% |

500 mg SCG, 150 mg of the ionic polymer IP 5 and 10 ml of H₂O were placed in a reactor, sealed and the reaction mixture was then heated at 180° C. for 2 hours. After reaction the mixture was cooled to RT, diluted with water (50 ml) and filtered for further analysis. The obtained products (% per 100 mg of initial coffee loading):

| | |
|---|---|
| Monosaccharides | 6.88% |
| Disaccharides | 2.04% |
| Trisaccharides | 0.55% |
| HMF | 1.2% |

Figure 3:
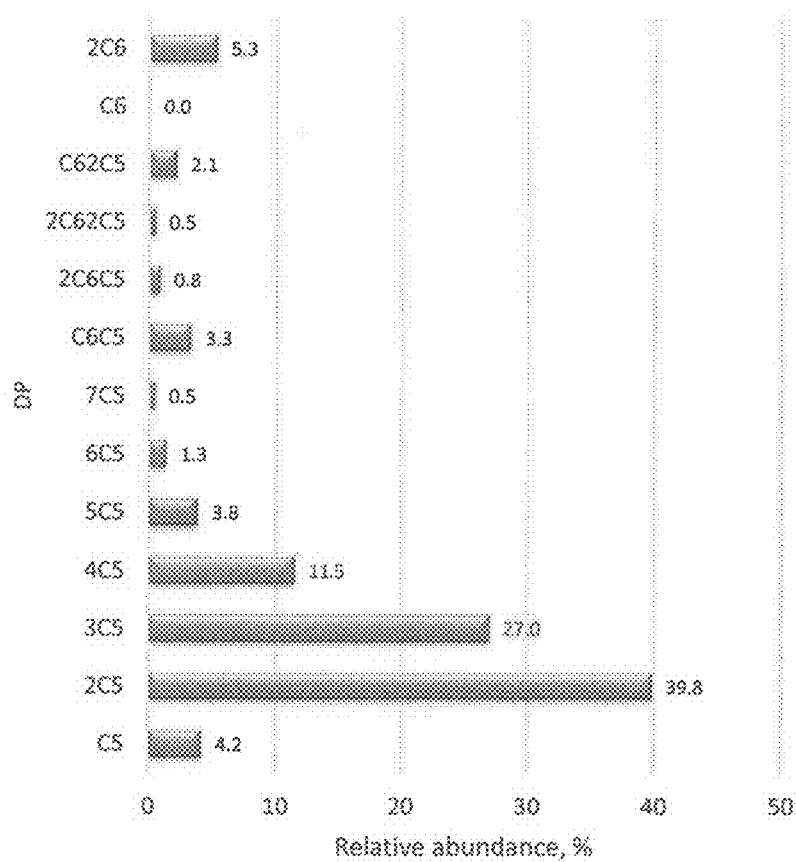
FIG. 3 shows the mono and oligosaccharides (50% yield) with the oligomers distribution (Cornstover transformations into mono and oligosaccharides).

Cornstover Transformations into Mono and Oligosaccharides 10 g of cornstover were mixed with 100 mg of IP 3 and 100 ml of H₂O for 45 min at 175° C. After reaction, the mixture was cooled to room temperature, diluted with water and filtered for further analysis. The mono and oligosaccharides (50% yield) with the oligomers distribution are shown in FIG. 3.

Figure 4:
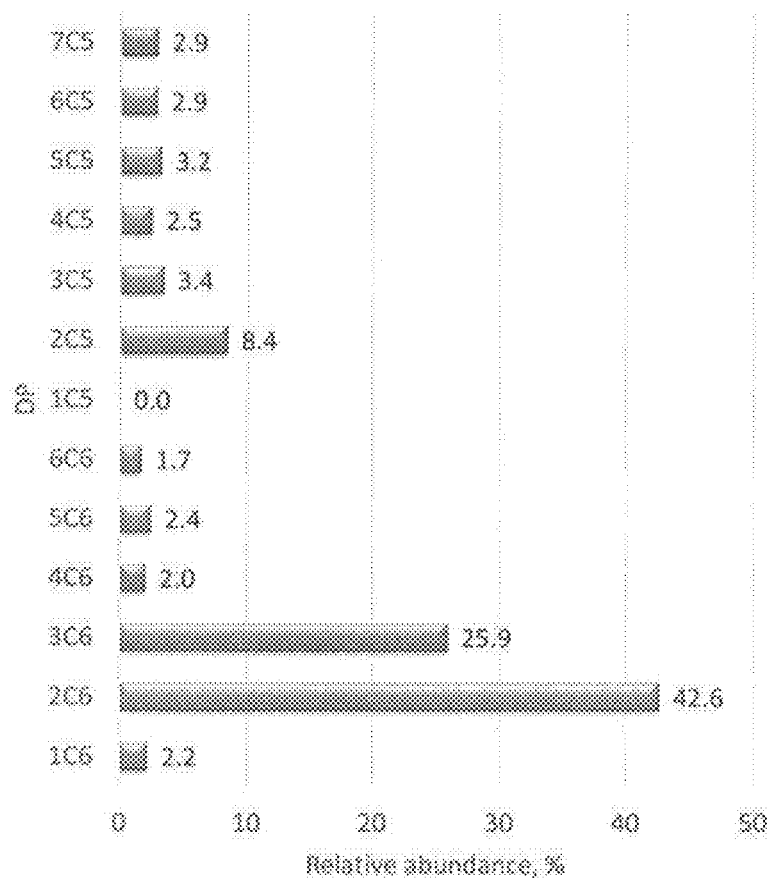
FIG. 4 shows the mono and oligosaccharides (55% yield) with the oligomers distribution (Rice husk transformations into mono and oligosaccharides).

Rice Husk Transformations into Mono and Oligosaccharides 10 g of rice husk were mixed with 200 mg of IP 1 and 150 ml of H₂O for 1 h at 160° C. After reaction, the mixture was cooled to room temperature, diluted with water and filtered for further analysis. The mono and oligosaccharides (55% yield) with the oligomers distribution are shown in FIG. 4. In addition, 3 wt % of the final product were assigned as polyphenols.

Figure 5:
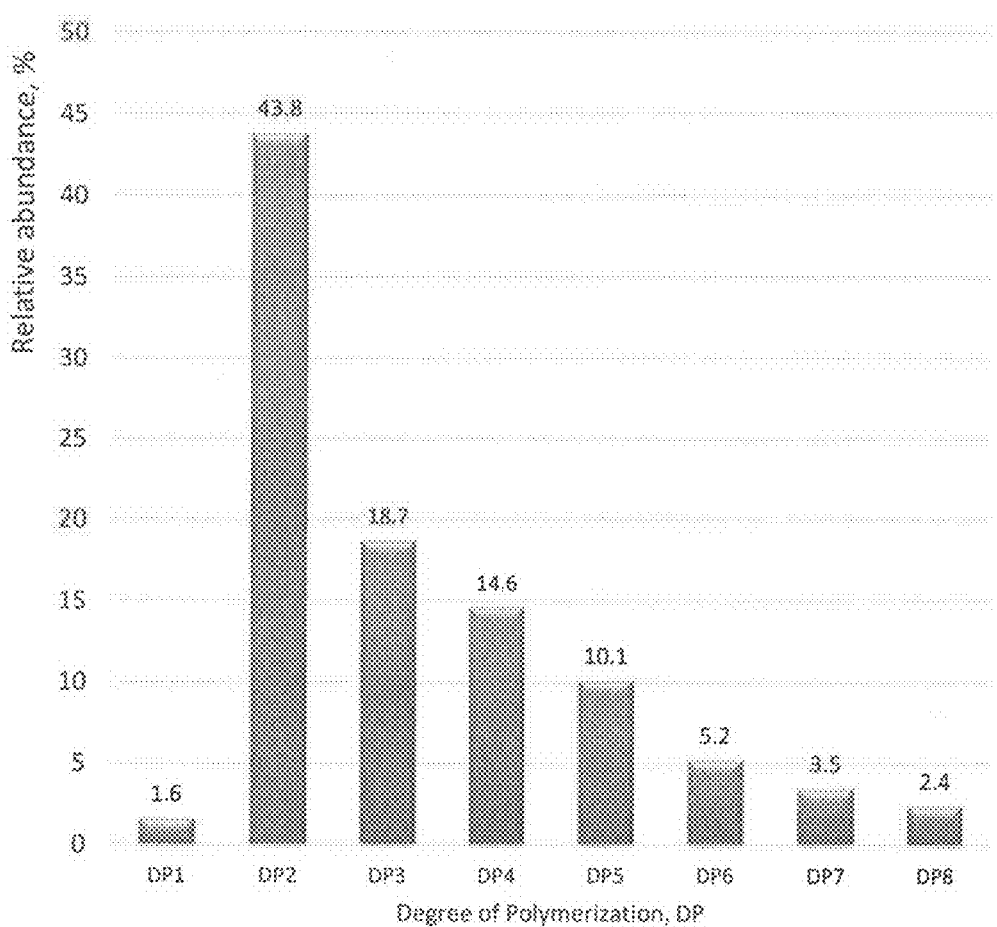
FIG. 5 shows the mono and oligosaccharides (92% yield) with the oligomers distribution (Yeast cell wall transformations into mono and oligosaccharides).

Yeast Cell Wall Transformations into Mono and Oligosaccharides 10 g of cornstover were mixed with 50 mg of IP 3 and 100 ml of H₂O for 1 h at 160° C. After reaction, the mixture was cooled to room temperature, diluted with water and filtered for further analysis. The mono and oligosaccharides (92% yield) with the oligomers distribution are shown in FIG. 5.

Figure 6:
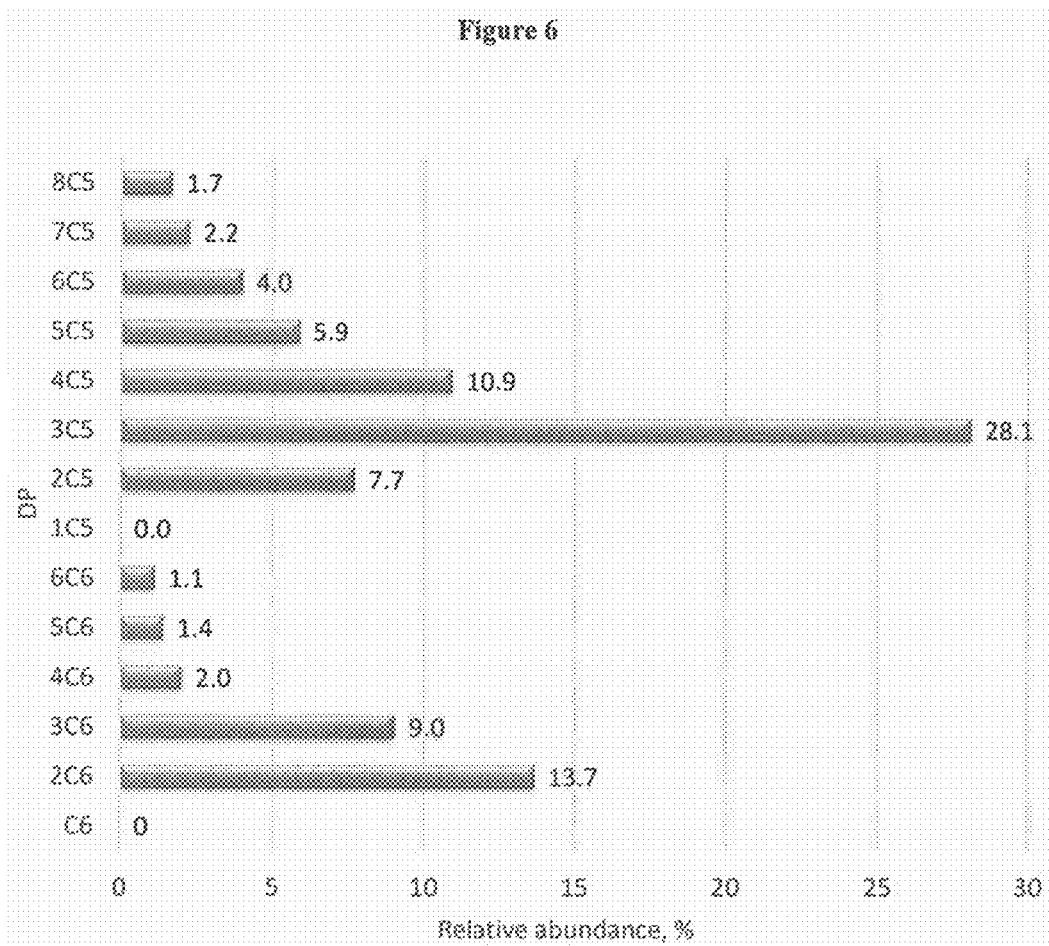
FIG. 6 shows the mono and oligosaccharides (55% yield) with the oligomers distribution (SBG transformation).
Figure 7:
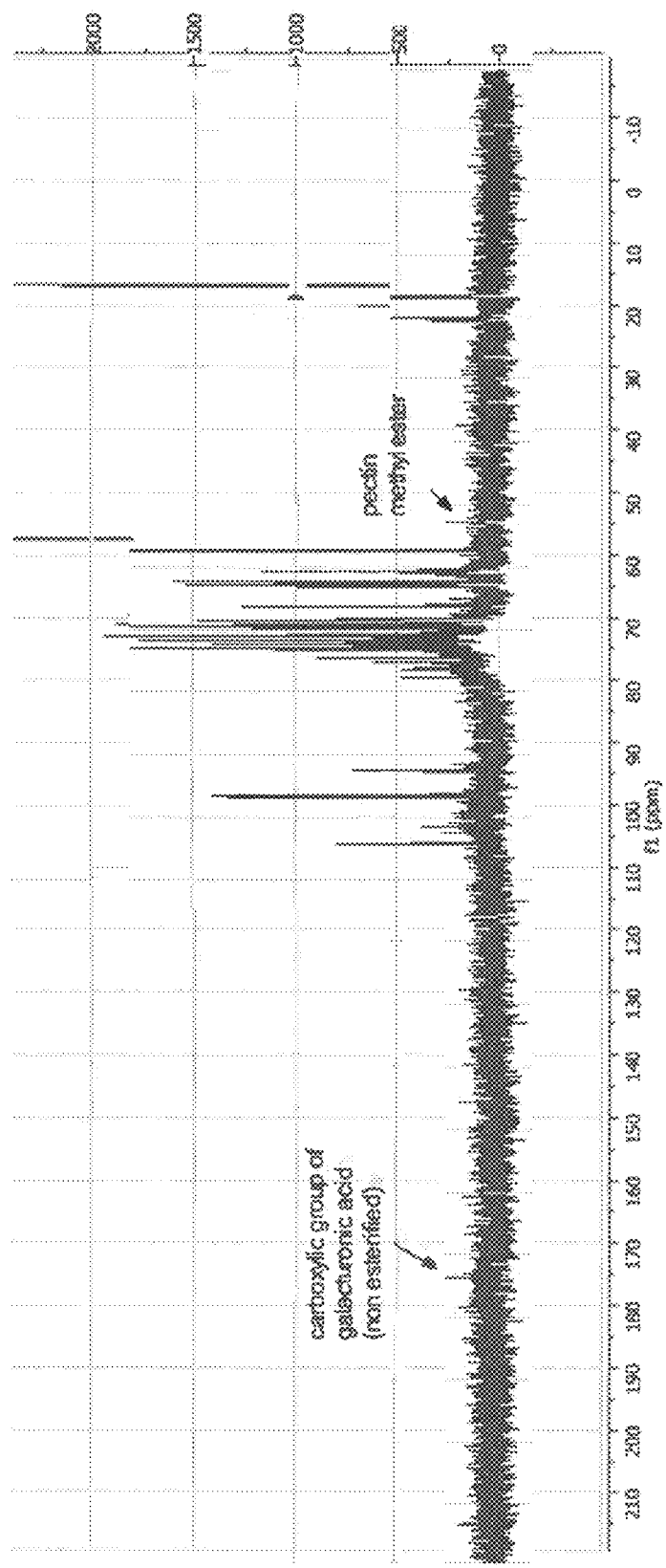
FIG. 7 shows $^{13}$C NMR spectrum of the product obtained from apple pomace.

SBG Transformations 10 g of spent brewery grains were mixed with 200 mg of IP 1 and 150 ml of H₂O for 1 h at 150° C. After reaction, the mixture was cooled to room temperature, diluted with water and filtered for further analysis. The mono and oligosaccharides (55% yield) with the oligomers distribution are shown in FIG. 6. In addition, 0.2 wt % of the final product were assigned as ferulic compounds.

Apple Pomace Transformations 10 g of apple pomace were mixed with 200 mg of IP 1 and 100 ml of H₂O for 1 h at 160° C. After reaction, the mixture was cooled to room temperature, diluted with water and filtered for further analysis.

We claim:

1. An ionic polymer (IP) consisting of a first monomer of formula I

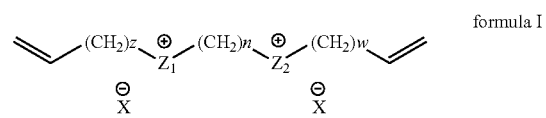

formula I or consisting of a first monomer of formula I

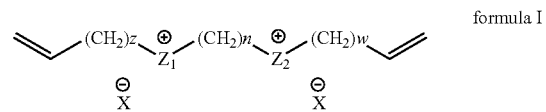

formula I and at least one second monomer selected from the group consisting of

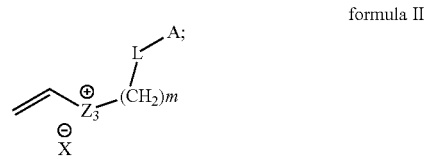

formula II

formula III

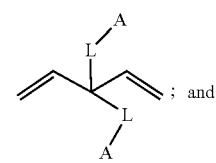

formula IV wherein n and m are independently selected from 1, 2, 3, 4, 5, 6;

z and w are independently selected from 0, 1, 2, 3;

$Z_1$, $Z_2$ and $Z_3$ are cations each independently selected from the group consisting of:

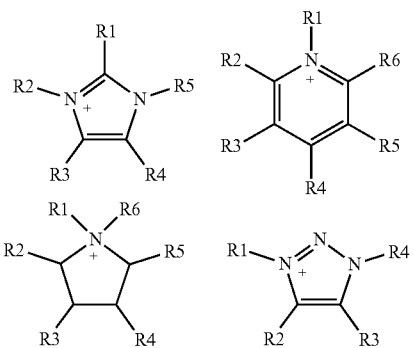

37
-continued

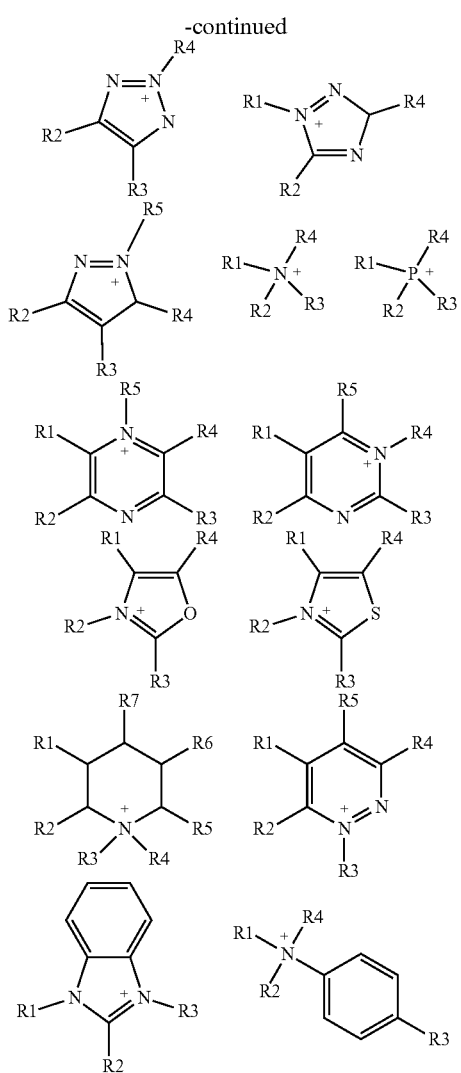

R1, R2, R3, R4, R5, R6 and R7 are each independently selected from the group consisting of a bond, H, $C_1$-$C_6$ alkyl, allyl, —$CH_2$—$(CH_2)_p$—O—$(CH_2)_q$—$CH_3$, $C_1$-$C_6$ alkoxy, $C_1$-$C_6$ alkoxyalkyl, benzyl, —$SO_3H$, and —$(CH_2)_q$—$SO_3H$, provided that two of R1, R2, R3, R4, R5, R6 and R7 are each a bond;
p and q are independently selected from 0, 1, 2, 3, 4, 5, 6;
L is an optional linker and each occurrence of L, if present, is independently selected from the group consisting of substituted or unsubstituted $C_1$-$C_{20}$ alkylene, alkenylene, alkynylene and substituted or unsubstituted $C_5$-$C_{10}$ aryl, wherein the substituents are selected from the group consisting of H, —$SO_3H$, —COOH, —[P(=O)(OH)$_2$], —[P(=O)(OH)], —O—$SO_3H$, -O—COOH, —O—[P(=O)(OH)$_2$], and —O—[P(=O)(OH)];
A is an optional acidic group and each occurrence of A, if present, is independently selected from the group consisting of —$SO_3H$, —COOH, —[P(=O)(OH)$_2$], —[P(=O)(OH)], —O—$SO_3H$, —O—COOH, —O—[P(=O)(OH)$_2$], —O—[P(=O)(OH)], and —$CH_2$—COOH;
$X^-$ is selected from the group consisting of $F^-$, $Cl^-$, $Br^-$, $I^-$, $ClO_4^-$, $BF_4^-$, $PF_6^-$, $AsF_6^-$, $SbF_6^-$, $NO_2^-$, $NO_3^-$, 38
$HSO_4^-$, $SO_4^{2-}$, $PO_4^{3-}$, $HPO_4^{2-}$, $CF_3CO_2^-$, $CF_3CO_3^-$, $CO_3^{2-}$, $CF_3SO_3^-$, $C_1$-$C_6$ carboxylate, $CN^-$, $SCN^-$, $OCN^-$, $CNO^-$, $N_3^-$, tosylate, mesylate, trifluoroethane sulfonate, di-trifluoromethanesulfonyl amino, docusate, and xylenesulfonate.

2. The ionic polymer (IP) of claim 1, wherein
n is 1 or 2,
m is 1 or 2,
z and w are 0 or 1,
$Z_1$, $Z_2$ and $Z_3$ are cations each independently selected from the group consisting of:

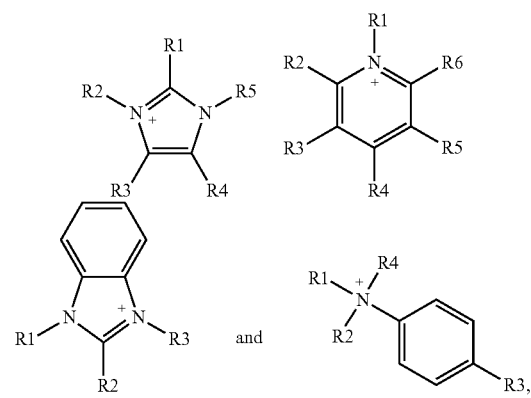

R1, R2, R3, R4, R5, R6 and R7 are each independently selected from the group consisting of a bond, H, and $C_1$-$C_6$ alkyl, provided that two of R1, R2, R3, R4, R5, R6 and R7 are each a bond,
A, if present, is independently selected from the group consisting of H, —$SO_3H$, —COOH, —O—COOH, and —$CH_2$—COOH,
$X^-$ is selected from the group consisting of $F^-$, $Cl^-$, $HSO_4^-$, $SO_4^{2-}$, $PO_4^{3-}$, $HPO_4^{2-}$, $CF_3CO_2^-$, $CF_3CO_3^-$, and $CF_3SO_3^-$.

3. The ionic polymer (IP) of claim 1, wherein L is absent.

4. The ionic polymer (IP) of claim 1, wherein A is absent or A is independently selected from the group consisting of H, —COOH, and —$CH_2$—COOH.

5. The ionic polymer (IP) of claim 1, wherein $Z_1$ and $Z_2$ are the same.

6. The ionic polymer (IP) of claim 1, wherein $C_1$-$C_6$ carboxylate are selected from the group consisting of formate, acetate, propionate, butyrate, hexanoate, maleate, fumarate, oxalate, lactate, and pyruvate.

7. The ionic polymer (IP) of claim 1, wherein the first monomer according to formula I is selected from the group consisting of

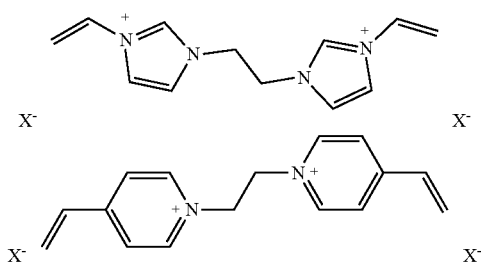

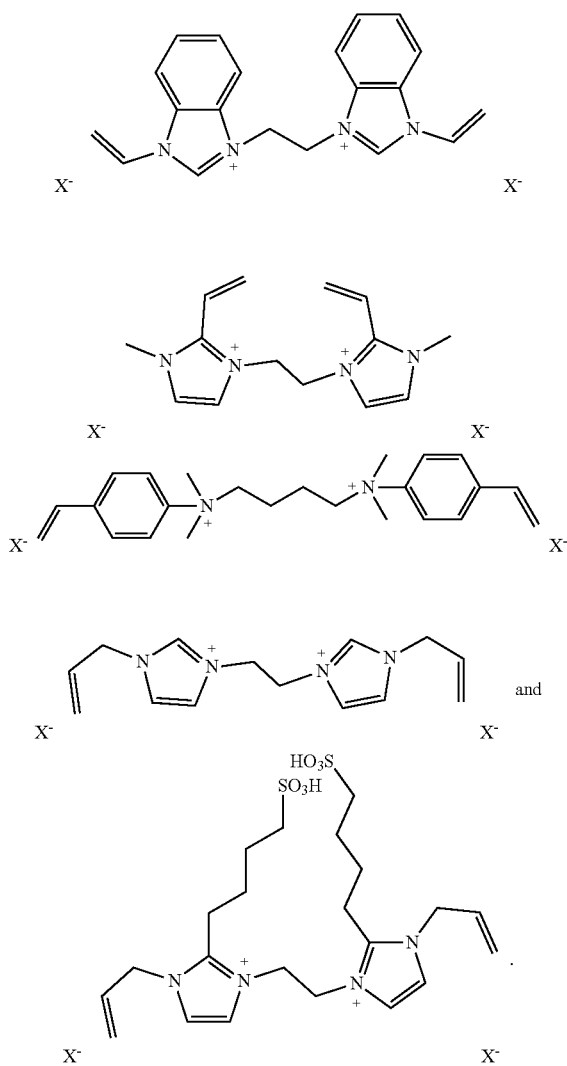

8. The ionic polymer (IP) of claim 1, wherein the second monomer according to formula II is

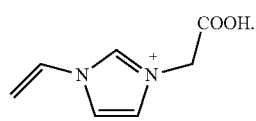

9. The ionic polymer (IP) of claim 1 selected from the group consisting of

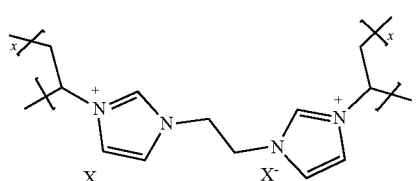

IP 1: X = Cl⁻
IP 2: X = CF₃SO₃⁻

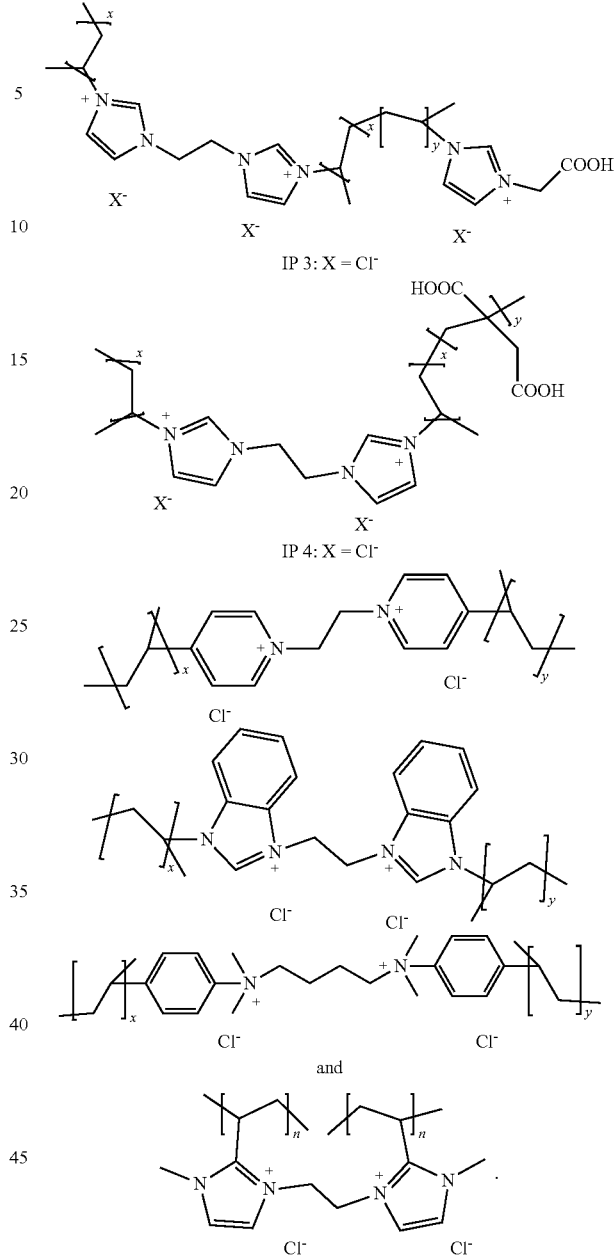

10. An ionic polymer network comprising cross-linked one or more ionic polymers of claim 1.

11. A solid support having at least one surface comprising one or more ionic polymers of claim 1 or the ionic polymer network of claim 10.

12. A polymer membrane incorporating one or more ionic polymers of claim 1 or the ionic polymer network of claim 10.

13. A method for producing one or more fine chemicals selected from the group consisting of lipids, sugars, furanic compounds, humins, polyphenols and pectic compounds from biomass, the method comprising the steps of:
 a) providing biomass;
 b) optionally determining lipids and/or sugars contents in the biomass;
 c) optionally pretreating the biomass;
 d) contacting the biomass with a catalyst to form a reaction mixture, wherein the catalyst is an ionic polymer of claim 1 or a combination of ionic polymers of claim 1, the ionic polymer network of claim 10, a solid-supported ionic polymers of claim 11 and/or a membrane of claim 12;

e) degrading the biomass in the reaction mixture to produce a liquid phase and a solid phase, wherein the liquid phase includes the one or more fine chemicals, and the solid phase includes residual biomass;

f) isolating at least a portion of the liquid phase from the solid phase; and g) recovering the one or more fine chemicals from the isolated liquid phase.

14. The method of claim 13, wherein the step d) consists in adding water or organic solvent and an effective amount of the catalyst to the biomass to form a reaction mixture, and degrading step e) consists in heating the reaction mixture of step d) and subsequently cooling to room temperature.

15. The method of claim 13, wherein the fine chemical is sugar.

16. A method for producing C5 and C6 sugars, furfural, 5-hydroxymethylfurfural (HMF) and derivatives of HMF from biomass selected from the group consisting of alkoxymethylfurfurals and haloalkylfurfurals, the method comprising the steps of:

a) providing biomass;

b) optionally determining sugars contents in the biomass;

c) optionally pretreating the biomass;

d) contacting the biomass with a catalyst to form a reaction mixture, wherein the catalyst is an ionic polymer of claim 1 or a combination of ionic polymers of claim 1, the ionic polymer network of claim 10, a solid-supported ionic polymers of claim 11 and/or a membrane of claim 12;

e) degrading the biomass in the reaction mixture to produce a first liquid phase and a first solid phase, wherein the first liquid phase includes C5 oligomer sugars and/or C5 monomer sugars and can further include furfural if the time of degrading step is extended, and the first solid phase includes residual material;

f) isolating at least a portion of the first liquid phase from the first solid phase;

g) recovering C5 oligomer sugars and/or C5 monomer sugars and/or furfural from the isolated first liquid phase;

h) contacting the first solid phase that includes residual material with the same catalyst as in step d) or with a different catalyst, to form a reaction mixture, wherein the catalyst is an ionic polymer of claim 1 or a combination of ionic polymers of claim 1, the ionic polymer network of claim 10, a solid-supported ionic polymers of claim 11 and/or a membrane of claim 12;

i) further degrading the first solid phase that includes residual material in the reaction mixture to produce a second liquid phase and a second solid phase, wherein the second liquid phase includes C6 oligomer sugars and/or C6 monomer sugars and can further include 5-hydroxymethylfurfural (HMF) and derivatives of HMF and/or humins if the time of degrading step is extended, and the second solid phase includes residual material;

j) isolating at least a portion of the second liquid phase from the second solid phase; and k) recovering C6 oligomer sugars and/or C6 monomer sugars and/or 5-hydroxymethylfurfural (HMF) and derivatives of HMF and/or humins from the isolated second liquid phase.

17. The method of claim 16, wherein the step d) consists in adding water or organic solvent and an effective amount of the catalyst to the biomass to form a reaction mixture, and degrading steps e) and i) consist in heating the reaction mixture and subsequently cooling to room temperature.

18. The method of claim 13, wherein the biomass is selected from the group consisting of cellulosic, chitinous, oleaginous or lignocellulosic material.

19. The ionic polymer of claim 1, wherein L is a $C_3$-$C_{20}$ alkylene, $C_1$-$C_{20}$ alkenylene, $C_1$-$C_{20}$ alkynylene, or substituted or unsubstituted $C_5$-$C_{10}$ aryl, wherein the substituents are selected from the group consisting of H, —$SO_3H$, —COOH, —[P(=O)(OH)$_2$], —[P(=O)(OH)], —O—$SO_3H$, —O—COOH, —O—[P(=O)(OH)$_2$], and —O—[P(=O)(OH)].

20. The ionic polymer of claim 1, wherein $Z_1$, $Z_2$ and $Z_3$ are each independently

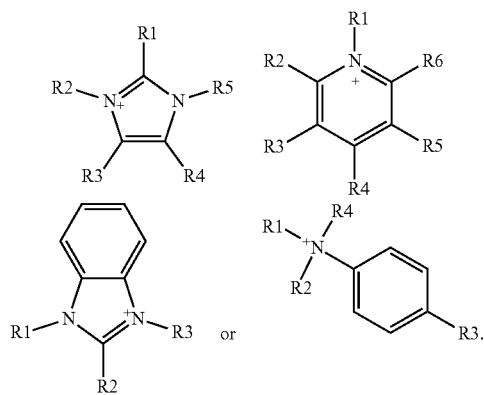

21. The ionic polymer of claim 1, wherein n is 1 or 2.

22. The ionic polymer of claim 1, wherein $X^-$ is selected from the group consisting of $F^-$, $Cl^-$, $Br^-$, $I^-$, $ClO_4^-$, $BF_4^-$, $PF_6^-$, $AsF_6^-$, $SbF_6^-$, $NO_2^-$, $NO_3^-$, $SO_4^{2-}$, $PO_4^{3-}$, $HPO_4^{2-}$, $CF_3CO_2^-$, $CF_3CO_3^-$, $CO_3^{2-}$, $CF_3SO_3^-$, $C_1$-$C_6$ carboxylate, $CN^+$, $SCN^+$, $OCN^+$, $CNO^+$, $N_3^-$, tosylate, mesylate, trifluoroethane sulfonate, di-trifluoromethanesulfonyl amino, docusate, and xylenesulfonate; and wherein L is a substituted or unsubstituted $C_1$-$C_{20}$ alkylene, alkenylene, alkynylene and substituted or unsubstituted $C_5$-$C_{10}$ aryl, wherein the substituents are selected from the group consisting of H, —COOH, —[P(=O)(OH)$_2$], —[P(=O)(OH)], —O—$SO_3H$, —O—COOH, —O—[P(=O)(OH)$_2$], and —O—[P(=O)(OH)]; or wherein A is an optional acidic group and each occurrence of A, if present, is independently selected from the group consisting of —COOH, —[P(=O)(OH)$_2$], —[P(=O)(OH)], —O—$SO_3H$, —O—COOH, —O—[P(=O)(OH)$_2$], —O—[P(=O)(OH)], and —$CH_2$—COOH.

* * * * *